(12) United States Patent
Pincelli et al.

(10) Patent No.: US 9,255,150 B2
(45) Date of Patent: Feb. 9, 2016

(54) REMEDIES FOR PEMPHIGUS CONTAINING ANTI-FAS LIGAND ANTIBODIES

(75) Inventors: Carlo Pincelli, Sassuolo (IT); Alessandra Marconi, Reggio Emilia (IT)

(73) Assignee: PINCELL SRL, Modena (IT)

( * ) Notice: Subject to any disclaimer, the term of this patent is extended or adjusted under 35 U.S.C. 154(b) by 26 days.

(21) Appl. No.: 13/139,048

(22) PCT Filed: Dec. 14, 2009

(86) PCT No.: PCT/EP2009/067129
§ 371 (c)(1),
(2), (4) Date: Jun. 10, 2011

(87) PCT Pub. No.: WO2010/066914
PCT Pub. Date: Jun. 17, 2010

(65) Prior Publication Data
US 2011/0243946 A1 Oct. 6, 2011

(30) Foreign Application Priority Data
Dec. 12, 2008 (EP) .................. PCT/EP2008/010597

(51) Int. Cl.
*A61K 39/395* (2006.01)
*C07K 16/28* (2006.01)
*A61K 39/00* (2006.01)

(52) U.S. Cl.
CPC ........ *C07K 16/2875* (2013.01); *A61K 2039/505* (2013.01); *C07K 2317/21* (2013.01); *C07K 2317/74* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,114,507 A * | 9/2000 | Shirakawa et al. | |
| 6,777,540 B1 | 8/2004 | Okumura et al. | |
| 6,946,255 B1 | 9/2005 | Kayagaki et al. | |
| 7,262,277 B2 | 8/2007 | Lancaster | |
| 2005/0106140 A1 | 5/2005 | Lancaster | |
| 2011/0038867 A1 | 2/2011 | Princelli et al. | |
| 2011/0173277 A1 | 7/2011 | Cordani et al. | |

FOREIGN PATENT DOCUMENTS

| | | |
|---|---|---|
| CN | 1642980 | 7/2005 |
| EP | 0 842 948 | 5/1998 |
| EP | 0 957 166 | 11/1999 |
| WO | WO 97/02290 | 1/1997 |
| WO | WO-03 079750 | 10/2003 |

(Continued)

OTHER PUBLICATIONS

Olivry et al., Dermatoses affecting desmosomes in animals; a mechanistic review of acantholytic blistering skin diseases, Vet. Dermatol. 20:313-326, 2009.*

(Continued)

*Primary Examiner* — Claire Kaufman
(74) *Attorney, Agent, or Firm* — Millen, White, Zelano, Branigan, P.C.

(57) ABSTRACT

The present invention refers to the use of FasL antagonists, e.g. of humanized antibodies directed against human Fas ligands (also named CD95L or Apo1L and hereinafter abbreviated as FasL) for the prevention and/or treatment of skin diseases associated with keratinocytes acantholysis, particularly for the prevention and/or treatment of pemphigus.

14 Claims, 15 Drawing Sheets

(56) References Cited

FOREIGN PATENT DOCUMENTS

| WO | WO-2009 074339 | 6/2009 |
| WO | WO 2010/006914 | 1/2010 |

OTHER PUBLICATIONS

Obungu et al., Determination of the mechanism of action of antiFasL antibody by epitope mapping and homology modeling, Biochem. 48:7251-7260, 2009.*
Nisihara et al., Humanization and epitope mapping of neutralizing anti-human fas ligand monoclonal antibodies: structural insightes into Fas/Fas Ligand interaction, J. Immunol. 167:3266-3275, 2001.*
Baker et al., Specificity questions concerning the clone ee anti-fas ligand antibody, Cell Death Diff. 7(1):Jan. 8-9, 2000.*
Kunik et al., Structural consensus among antibodies defines the antigen binding site, PLoS Computational Biology, 8(2):e1002388 (p. 1-12), Feb. 2012.*
Arredondo, J. et al., "Novel Mechanisms of Target Cell Death and Survival and of Therapeutic Action of IVIg in Pemphigus," American Journal of Pathology, Dec. 2005, vol. 167, No. 6, pp. 1531-1544.
Byers, T., "What can randomized controlled trials tell us about nutrition and cancer prevention?" CA Cancer J Clin., 1999, vol. 49, pp. 353-361.
Casset, F. et al., "A peptide mimetic of an anti-CD4 monoclonal antibody by rational design," Biochemical and Biophysical Research Communications, 2003, vol. 307, pp. 198-205.
Chen, Y. et al., "Selection and Analysis of an Optimized Anti-VEGF Antibody: Crystal Structure of an Affinity-matured Fab in Complex with Antigen," J. Mol. Biol. 1999, vol. 293, pp. 865-881.
De Pacalis, R. et al., "Grafting of 'Abbreviated' Complementarity-determining regions containing specificity-determining residues Essential for Ligand Contact to Engineer a Less Immunogenic Humanized Monoclonal Antibody," The Journal of Immunology, 2002, vol. 169, pp. 3076-3084.
Grando, S. A. et al., "Apoptolysis: a novel mechanism of skin blistering in pemphigus vulgaris linking the apoptotic pathways to basal cell shrinkage and suprabasal acantholysis," Experimental Dermatology, 2009, vol. 18, pp. 764-770.
Harlow, E. et al., "Epitope Mapping by Competition Assay," Using Antibodies, Chapter 11, 1999.
Holm, P. et al., "Functional mapping and single chain construction of the anti-cytokeratin 8 monoclonal antibody TS1," Molecular Immunology, 2007, vol. 44, pp. 1075-1084.
Kwak, J. et al., "A convenient method for epitope competition analysis of two monoclonal antibodies for their antigen binding," Journal of Immunological Methods, 1996, vol. 191, pp. 49-54.
MacCallum, R. M. et al., "Antibody-Antigen Interactions: Contact Analysis and Binding Site Topography," J. Mol. Biol., 1996, vol. 262. pp. 732-745.
Office Action for Related Chinese Patent Application No. 200880124180.7 dated Aug. 1, 2012, Do not Print.
Office Action for Related Russian Patent Application No. 2010 128 556 dated Sep. 18, 2012, Do not Print.
Roitt, A. et al., Immunology, pp. 110 , (6th Ed.,Mosby:Edinburgh), 2001.
Rudikoff, S. et al., "Single amino acid substitution altering antigen-binding specificity," Proc. Natl. Acad. Sci., Mar. 1982, vol. 79, pp. 1979-1983.
Skolnick, J. et al., "From genes to protein structure and function: novel applications of computational approaches in the genomic era," Trends in Biotechnology, Jan. 2000, vol. 18, pp. 34-39.
Vajdos, F. F. et al., "Comprehensive Functional Maps of the Antigen-binding Site of an Anti-ErbB2 Antibody Obtained with Shotgun Scanning Mutagenesis," J. Mol. Biol., 2002, vol. 320, pp. 415-428.
Viard, S. et al., "Inhibition of Toxic Epidermal Necrolysis by Blockade of CD95 with Human Intravenous Immunoglobulin," Science, Oct. 16, 1988, vol. 282, No. 5388, pp. 490-493.
Wang, X. et al., "Possible apoptotic mechanism in epidermal cell acantholysis induced by pemphigus vulgaris autoimmunoglobulins," Apoptosis, 2004, vol. 9, pp. 131-143.
Weseem, N. H. et al., "Monoclonal antibody analysis of the proliferating cell nuclear antigen (PCNA): Structural conservation and the detection of a nucleolar form," Journal of Cell Science, 1990, vol. 96, pp. 121-129.
Wu, H. et al., "Humanization of a Murine Monoclonal Antibody by Simultaneous Optimization of Framework and CDR Residues," J. Mol. Biol. 1999, vol. 294, pp. 151-162.
Ahmed, A. R., "Intravenous immunoglobulin therapy in the treatment of patients with pemphigus vulgaris unresponsive to conventional immunosuppressive treatment," J. Am. Acad. Dermatol., Nov. 2001, vol. 45, No. 5, pp. 679-690.
International Search Report for PCT/EP2009/067129 dated Jun. 25, 2007.
Morrison, L. H., "Therapy of refractory pemphigus vulgaris with monoclonal anti-CD20 antibody (rituximab)," J. Am. Acad. Dermatol., Nov. 2004, vol. 51, No. 5, pp. 317-319.
Puviani, M. et al., "Fas ligand in pemphigus sera induces keratinocyte apoptosis through the activation of caspase-8," The Journal of Investigative Dermatology, Jan. 2003, vol. 120, No. 1, pp. 164-167.
International Search Report of PCT/EP2008/010597—Apr. 29, 2009.
Aoudjit, F. et al., "Matrix attachment regulates FAS-induced apoptosis in endothelial cells: a role for c-FLIP and implications for anoikis", J Cell Blol, 2001, vol. 152, pp. 633-643.
Cirillo, N. et al., "Searching for experimental models of Pemphigus vulgaris" Archives of Dermatologival Research (2007); 299(1): pp. 9-12.
Granziero Et Al., Adoptive immunotherapy prevents prostate cancer in a transgenic mouse model. European Journal of Immunology, 1999, vol. 29, pp. 1127-1138.
Schaub et al.: "Fas and Fas-associated death domain protein regulate monocyte chermattractant protein-1 expression by human smooth muscle cells through caspase- and calpain-dependent release of interleukin-1$\alpha$", Circulation Research, Sep. 19, 2003, pp. 515-522.
Estaquier et al.: "Fas-mediated apoptosis of CD4+ and CD8+ T cells from human immunodeficiency virus-infected persons: differential in vitro preventive effect of cytokines and protease antagonists", Blood, Jun. 15, 1996, vol. 87, No. 12, pp. 4959-4966.
Purevjav et al.: "Myocardial Fas ligand expression increases susceptibility to AZT-induced cardiomyopathy", Cardiovasc. Toxicol., 2007, vol. 7, pp. 255-263.
Reipert, B. M.: "Variation of anti-Fas antibodies in different lots of intravenous immunoglobulin", Vox Sanguinis, 2008, vol. 94, p. 334-341.
Anhalt et al., „Induction of pemphigus in neonatal mice by passive transfer of IgG from patients with the disease, The New England Journal of Medicine, vol. 306, No. 20, May 20, 1982, pp. 1189-1196.
Berkowitz et al., „p38MAPK inhibition prevents disease in pemphigus vulgaris mice, PNAS, Aug. 22, 2006, vol. 103, No. 34, 12855-12860.
Chen et al. „Duplicating autoimmune bullous diseases by passively transferring autoantibodies into animals, Milestones cutaneous biology, Oct. 2008, E25- E27.
Li et al., „Involvement of the apoptotic mechanisms in pemphigus foliaceus autoimmune injury of the skin, J. Immunol. Jan. 1, 2009, 182(1): 711-717.
Pretel et al., „An imbalance in Akt/mTOR is involved in the apoptotic and acantholytic processes in a mouse model of pemphigus vulgaris, Experimental Dermatology, 2009, 18, 771-780.
Lotti, R. et al. „A previously unreported function of $\beta$1B integrin isoform in caspase-8-dependent integrin-mediated keratinocyte death, Journal of Investigative Dermatology (2010) 130,2569-2577.
Dusek, R. et al., „The differentiation-dependent desmosomal cadherin desmoglein 1 is a novel capsase-3 target that regulates apoptosis in keratinocytes, J. Biol. Chem. 2006, 281:3614-3624.
French: "Toxic Epidermal Necrolysis and Stevens Johnson Syndrome: Our Current Understanding", Allergology International, vol. 55, 2006, pp. 9-16.

(56) References Cited

OTHER PUBLICATIONS

Nassif et al.: "Evaluation of the Potential Role of Cytokines in Toxic Epidermal Necrolysis", J. Invest. Dermatol., vol. 123, 2004, pp. 850-855.
Neppelberg et al.: "Short communication; Apoptosis in oral lichen planus", Eur. J. Oral . Sci., vol. 109, 2001, pp. 361-364.
Shaker et al.: "Role of apoptosis stimulus factor and its ligand in the induction of apoptosis in some ultraviolet-induced diseases", Dermatology Online Journal, vol. 12, No. 3, 2006, p. 4.
Viard-Leveugle et al.: "Intracellular Localization of Keratinocyte Fas Ligand Explains Lack of Cytolytic Activity under Physiological Conditions", The Journal of Biological Chemistry, vol. 278, No. 18, 2003, pp. 16183-16188.
Gilhar et al.: "The pathogenesis of lichen planus", British Journal of Dermatology, vol. 120, 1989, pp. 541-544.
Paul et al.: "Apoptosis as a mechanism of keratinocyte death in toxic epidermal necrolysis", British Journal of Dermatology, vol. 134, 1996, pp. 710-714.
Hadzi-Mihailovic et al.: "Expression of Fas/FasL in patients with oral lichen planus", Journal of BUON, vol. 14, 2009, pp. 487-493.
Leithäuser et al.: "Constitutive and Induced Expression of APO-1, A New Member of the Nerve Growth Factor/ Tumor Necrosis Factor Receptor Superfamily, In Normal and Neoplastic Cells", Laboratory Investigation, vol. 69, No. 4, 1993, pp. 415-429.
Zhai Zhonge et al. (Ed.), Cell Biology, Chinese High Education Press, Aug. 31, 2000, p. 461, paragraphs 4-5 [English translation].
Bachmann et al.: "Ultraviolet Light Downregulates CD95 Ligand and Trail Receptor Expression Facilitating Actinic Keratosis and Squamous Cell Carcinoma Formation", The Journal of Investigative Dermatology, vol. 117, No. 1, Jul. 1, 2001, pp. 59-66.
Berg et al.: "Enforced covalent trimerization increases the activity of the TNF ligand family members TRAIL and CD95L", Cell Death and Differentiation, vol. 14, 2007, pp. 2021-2034.
Danial et al.: "Cell Death: Critical Control Points", Cell, vol. 116, Jan. 23, 2004, pp. 205-219.
Farley et al.: "Fas Ligand Elicits a Caspase-Independent Proinflammatory Response in Human Keratinocytes: Implications for Dermatitis", Journal of Investigative Dermatology, vol. 126, 2006, pp. 2438-2451.
Hill et al.: "Fas Ligand: A Sensor for DNA Damage Critical in Skin Cancer Etiology", Science, vol. 285, Aug. 6, 1999, pp. 898-900.
Holler et al.: "Two Adjacent Trimeric Fas Ligands are Required for Fas Signaling and Formation of a Death-Inducing Signaling Complex", Molecular and Cellular Biology, vol. 23, No. 4, Feb. 2003, pp. 1428-1440.
Itoh et al.: "A Novel Protein Domain Required for Apoptosis", The Journal of Biological Chemistry, vol. 268, No. 15, May 25, 1993, pp. 10932-10937.
Kischkel et al.: "Cytotoxicity-dependent APO-1 (Fas/CD95)-associated proteins form a death-inducing signaling complex (DISC) with the receptor", The EMBO Journal, vol. 14, No. 22, 1995, pp. 5579-5588.
Langley et al.: "Apoptosis is the mode of keratinocyte death in cutaneous graft-versus-host disease", Journal of the American Academy of Dermatology, vol. 35, No. 2, part 1, Aug. 1996, pp. 187-190.
Leverkus et al.: "Fas/Fas Ligand Interaction Contributes to UV-Induced Apoptosis in Human Keratinocytes", Experimental Cell Research, vol. 232, 1997, pp. 255-262.
Muzio et al.: "An Induced Proximity Model for Caspase-8 Activation", The Journal of Biological Chemistry, vol. 273, No. 5, Jan. 30, 1998, pp. 2926-2930.
Tartaglia et al.: "Ligand Passing: The 75-kDa Tumor Necrosis Factor (TNF) Receptor Recruits TNF for Signaling by the 55-kDa TNF Receptor", The Journal of Biological Chemistry, vol. 268, No. 25, Sep 5, 1993, pp. 18542-18548.
Taylor et al.: "Apoptosis: controlled demolition at the cellular level", Nature Reviews, Molecular Cell Biology, vol. 9, Mar. 2008, pp. 231-241.
Trautmann et al.: "The Differential Fate of Cadherins during T-Cell-Induced Keratinocyte Apoptosis Leads to Spongiosis in Eczematous Dermatitis", The Journal of Investigative Dermatology, vol. 117, No. 4, Oct. 2001, 927-934.
Matsue et al.: "Keratinocytes constitutively express the Fas antigen that mediates apoptosis in IFNγ-treated cultured keratinocytes", Arch. Dermatol. Res., vol. 287, 1995, pp. 315-320.
Urano et al.: "Establishing a Laboratory Animal Model From a Transgenic Animal: RasH2 Mice as a Model for Carcinogenicity Studies in Regulatory Science", Veterinary Pathology, vol. 49, No. 1, 2012, pp. 16-23.
Gil et al.: "Inhibition of FAK prevents blister formation in the neonatal mouse model of pemphigus vulgaris", Experimental Dermatology, vol. 21, 2012, pp. 254-259.
Kroemer et al.: "Classification of cell death: recommendations of the Nomenclature Committee on Cell Death 2009", Cell Death and Differentiation, vol. 16, 2009, pp. 3-11.
Schmidt et al.: "Apoptosis is not required for acantholysis in pemphigus vulgaris", Am. J. Physiol. Cell. Physiol., vol. 296, 2009, pp. C162-C172.
Bektas et al.: "A Pathophysiologic Role for Epidermal Growth Factor Receptor in Pemphigus Acantholysis", The Journal of Biological Chemistry, vol. 288, Mar. 29, 2013, pp. 9447-9456.
Cirillo et al.: "Urban legends: pemphigus vulgaris", Oral Diseases, vol. 18, 2012, pp. 442-458.
Muzio et al.: "FLICE, A Novel FADD-Homologous ICE/CED-3-like Protease, Is Recruited to the CD95 (Fas/APO-1) Death-Inducing Signaling Complex", Cell, vol. 85, Jun. 14, 1996, pp. 817-827.
Davidson et al; T Cell Receptor Ligation Triggers Novel Nonapoptotic Cell Death Pathways That are Fas-Independent or Fas-Dependent The Journal of Immunology vol. 169, Dec. 2002, pp. 6218-6290.
Official Action related to corresponding Russian Patent Application No. 2011128702 dated Aug. 28, 2014.
Robert C. Ladner "Mapping the Epitopes of Antibodies" Biotechnology and Genetic Engineering Reviews, [2007], 24:1, 32 pages.
English Translation of Office Action corresponding to CN Application No. 200980154517.3; dated Mar. 30, 2015.
Page 392 figure 16-5, "Introduction of Chemicobiology", edited by Ma Lin & Gu Lianquan, Chemical Industry Press, published on Feb. 28, 2006.

\* cited by examiner

Healthy control | Perilesional pemphigus without therapy

Healthy control    Perilesional pemphigus    Lesional pemphigus

Figure 4
Figure 4A
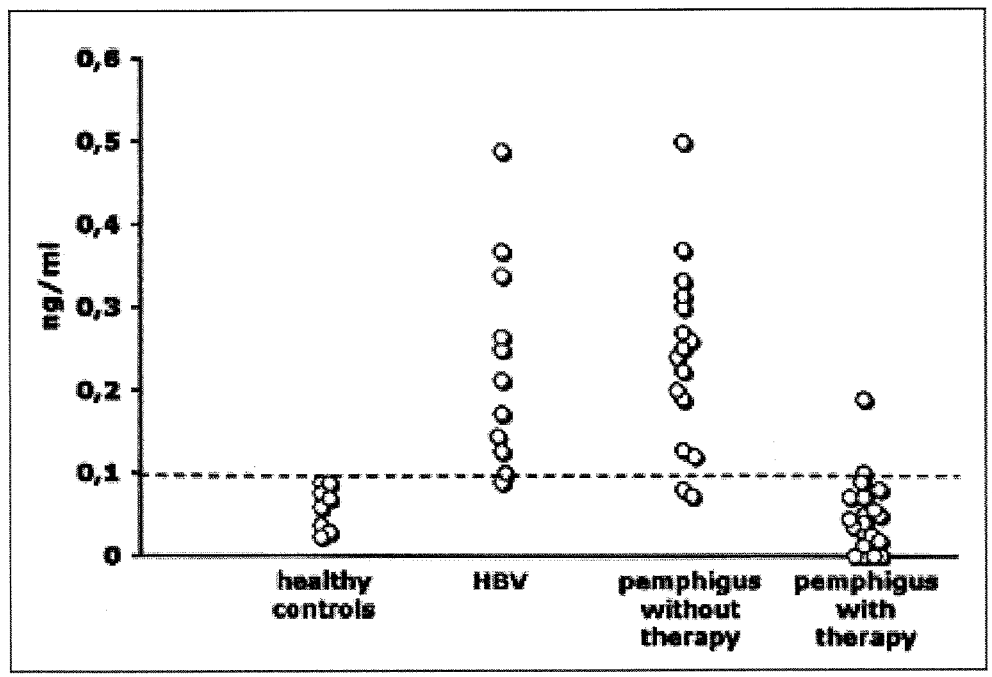
Figure 4B
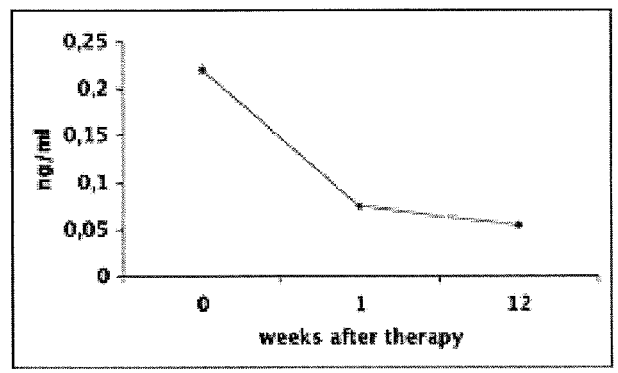

A

B

A

B

C

A

B

A

IHC

IHC

TUNEL

TUNEL procaspase-3
active fragment
Normal human IgG    PV human IgG active caspase-3

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial
<220> FEATURE:
<223> OTHER INFORMATION: Description of Artificial Sequence: Synthetic
      CDR H1 peptide

<400> SEQUENCE: 1

Asn Tyr Trp Ile Gly
1               5

<210> SEQ ID NO 2
<211> LENGTH: 17
<212> TYPE: PRT
<213> ORGANISM: Artificial
<220> FEATURE:
<223> OTHER INFORMATION: Description of Artificial Sequence: Synthetic
      CDR H2 peptide

<400> SEQUENCE: 2

Tyr Leu Tyr Pro Gly Gly Leu Tyr Thr Asn Tyr Asn Glu Lys Phe Lys
1               5                   10                  15

Gly

<210> SEQ ID NO 3
<211> LENGTH: 10
<212> TYPE: PRT
<213> ORGANISM: Artificial
<220> FEATURE:
<223> OTHER INFORMATION: Description of Artificial Sequence: Synthetic
      CDR H3 peptide

<400> SEQUENCE: 3

Tyr Arg Asp Tyr Asp Tyr Ala Met Asp Tyr
1               5                   10

<210> SEQ ID NO 4
<211> LENGTH: 16
<212> TYPE: PRT
<213> ORGANISM: Artificial
```

-continued

```
<220> FEATURE:
<223> OTHER INFORMATION: Description of Artificial Sequence: Synthetic
      CDR L1 peptide

<400> SEQUENCE: 4

Lys Ser Thr Lys Ser Leu Leu Asn Ser Asp Gly Phe Thr Tyr Leu Gly
1               5                   10                  15

<210> SEQ ID NO 5
<211> LENGTH: 7
<212> TYPE: PRT
<213> ORGANISM: Artificial
<220> FEATURE:
<223> OTHER INFORMATION: Description of Artificial Sequence: Synthetic
      CDR L2 peptide

<400> SEQUENCE: 5

Leu Val Ser Asn Arg Phe Ser
1               5

<210> SEQ ID NO 6
<211> LENGTH: 9
<212> TYPE: PRT
<213> ORGANISM: Artificial
<220> FEATURE:
<223> OTHER INFORMATION: Description of Artificial Sequence: Synthetic
      CDR L3 peptide

<400> SEQUENCE: 6

Phe Gln Ser Asn Tyr Leu Pro Leu Thr
1               5

<210> SEQ ID NO 7
<211> LENGTH: 5
<212> TYPE: PRT
<213> ORGANISM: Artificial
<220> FEATURE:
<223> OTHER INFORMATION: Description of Artificial Sequence: Synthetic
      CDR H1 peptide

<400> SEQUENCE: 7

Glu Tyr Pro Met His
1               5

<210> SEQ ID NO 8
<211> LENGTH: 17
<212> TYPE: PRT
<213> ORGANISM: Artificial
<220> FEATURE:
<223> OTHER INFORMATION: Description of Artificial Sequence: Synthetic
      CDR H2 peptide

<400> SEQUENCE: 8

Met Ile Tyr Thr Asp Thr Gly Glu Pro Ser Tyr Ala Glu Glu Phe Lys
1               5                   10                  15

Gly

<210> SEQ ID NO 9
<211> LENGTH: 8
<212> TYPE: PRT
<213> ORGANISM: Artificial
<220> FEATURE:
<223> OTHER INFORMATION: Description of Artificial Sequence: Synthetic
      CDR H3 peptide

<400> SEQUENCE: 9

Phe Tyr Trp Asp Tyr Phe Asp Tyr
```

<210> SEQ ID NO 10
<211> LENGTH: 11
<212> TYPE: PRT
<213> ORGANISM: Artificial
<220> FEATURE:
<223> OTHER INFORMATION: Description of Artificial Sequence: Synthetic
      CDR L1 peptide

<400> SEQUENCE: 10

Arg Ala Ser Gln Asp Ile Ser Asn Tyr Leu Asn
1               5                   10

<210> SEQ ID NO 11
<211> LENGTH: 7
<212> TYPE: PRT
<213> ORGANISM: Artificial
<220> FEATURE:
<223> OTHER INFORMATION: Description of Artificial Sequence: Synthetic
      CDR L2 peptide

<400> SEQUENCE: 11

Tyr Thr Ser Arg Leu His Ser
1               5

<210> SEQ ID NO 12
<211> LENGTH: 9
<212> TYPE: PRT
<213> ORGANISM: Artificial
<220> FEATURE:
<223> OTHER INFORMATION: Description of Artificial Sequence: Synthetic
      CDR L3 peptide

<400> SEQUENCE: 12

Gln Gln Gly Ser Thr Leu Pro Trp Thr
1               5

<210> SEQ ID NO 13
<211> LENGTH: 5
<212> TYPE: PRT
<213> ORGANISM: Artificial
<220> FEATURE:
<223> OTHER INFORMATION: Description of Artificial Sequence: Synthetic
      CDR H1 peptide

<400> SEQUENCE: 13

Arg His Gly Ile Thr
1               5

<210> SEQ ID NO 14
<211> LENGTH: 5
<212> TYPE: PRT
<213> ORGANISM: Artificial
<220> FEATURE:
<223> OTHER INFORMATION: Description of Artificial Sequence: Synthetic
      CDR H1 peptide

<400> SEQUENCE: 14

Ser His Gly Ile Ser
1               5

<210> SEQ ID NO 15
<211> LENGTH: 17
<212> TYPE: PRT
<213> ORGANISM: Artificial
<220> FEATURE:
<223> OTHER INFORMATION: Description of Artificial Sequence: Synthetic

```
                        CDR H2 peptide

<400> SEQUENCE: 15

Trp Ile Asn Ala Tyr Asn Gly Asn Thr Asn Tyr Ala Gln Lys Val Gln
1               5                   10                  15

Gly

<210> SEQ ID NO 16
<211> LENGTH: 17
<212> TYPE: PRT
<213> ORGANISM: Artificial
<220> FEATURE:
<223> OTHER INFORMATION: Description of Artificial Sequence: Synthetic
      CDR H2 peptide

<400> SEQUENCE: 16

Trp Ile Asn Ala Tyr Ser Gly Asn Thr Asn Tyr Ala Gln Lys Leu Gln
1               5                   10                  15

Gly

<210> SEQ ID NO 17
<211> LENGTH: 11
<212> TYPE: PRT
<213> ORGANISM: Artificial
<220> FEATURE:
<223> OTHER INFORMATION: Description of Artificial Sequence: Synthetic
      CDR H3 peptide

<400> SEQUENCE: 17

Glu Thr Met Val Arg Gly Val Pro Leu Asp Tyr
1               5                   10

<210> SEQ ID NO 18
<211> LENGTH: 11
<212> TYPE: PRT
<213> ORGANISM: Artificial
<220> FEATURE:
<223> OTHER INFORMATION: Description of Artificial Sequence: Synthetic
      CDR H3 peptide

<400> SEQUENCE: 18

Glu Thr Met Val Arg Gly Val Pro Cys Asp Tyr
1               5                   10

<210> SEQ ID NO 19
<211> LENGTH: 12
<212> TYPE: PRT
<213> ORGANISM: Artificial
<220> FEATURE:
<223> OTHER INFORMATION: Description of Artificial Sequence: Synthetic
      CDR L1 peptide

<400> SEQUENCE: 19

Arg Ala Ser Gln Ser Val Ser Ser Ser Tyr Leu Ala
1               5                   10

<210> SEQ ID NO 20
<211> LENGTH: 7
<212> TYPE: PRT
<213> ORGANISM: Artificial
<220> FEATURE:
<223> OTHER INFORMATION: Description of Artificial Sequence: Synthetic
      CDR L2 peptide

<400> SEQUENCE: 20

Gly Ala Ser Ser Arg Ala Thr
```

```
<210> SEQ ID NO 21
<211> LENGTH: 9
<212> TYPE: PRT
<213> ORGANISM: Artificial
<220> FEATURE:
<223> OTHER INFORMATION: Description of Artificial Sequence: Synthetic
      CDR L3 peptide

<400> SEQUENCE: 21

Gln Gln Tyr Gly Ser Ser Pro Trp Thr
1               5

<210> SEQ ID NO 22
<211> LENGTH: 4
<212> TYPE: PRT
<213> ORGANISM: Artificial
<220> FEATURE:
<223> OTHER INFORMATION: Description of Artificial Sequence: Synthetic
      caspase-8 inhibitor Z-IETD-FMK peptide
<220> FEATURE:
<223> OTHER INFORMATION: Z (Benzyloxycarbonyl) at N-terminus
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (4)..(4)
<223> OTHER INFORMATION: Methylation
<220> FEATURE:
<223> OTHER INFORMATION: FMK (Fluoromethylketone) at C-terminus

<400> SEQUENCE: 22

Ile Glu Thr Asp
1

<210> SEQ ID NO 23
<211> LENGTH: 120
<212> TYPE: PRT
<213> ORGANISM: Homo sapiens

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro
        115                 120

<210> SEQ ID NO 24
<211> LENGTH: 132
<212> TYPE: PRT
<213> ORGANISM: Homo sapiens
```

```
<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Arg His
            20                  25                  30

Gly Ile Thr Trp Val Arg Gln Ala Pro Gly Gln Gly Leu Glu Trp Met
            35                  40                  45

Gly Trp Ile Asn Ala Tyr Asn Gly Asn Thr Asn Tyr Ala Gln Lys Val
    50                  55                  60

Gln Gly Arg Val Thr Met Thr Thr Asp Lys Ser Thr Ser Thr Ala Tyr
65                  70                  75                  80

Met Glu Leu Arg Ser Leu Arg Ser Asp Asp Ala Ala Val Tyr Tyr Cys
                85                  90                  95

Ala Arg Glu Thr Met Val Arg Gly Val Pro Leu Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala
    130
```

REMEDIES FOR PEMPHIGUS CONTAINING ANTI-FAS LIGAND ANTIBODIES

SEQUENCE LISTING

The instant application contains a Sequence Listing which has been submitted electronically in ASCII format and is hereby incorporated by reference in its entirety. Said ASCII copy, created on Sep. 3, 2015, is named WEICKM-0092_SL.txt and is 8,041 bytes in size.

The present invention refers to the use of antagonists of human Fas ligand (also named CD95L or Apo1L and hereinafter abbreviated as FasL), more particularly to the use of humanized antibodies against FasL for the prevention and/or treatment of skin diseases associated with keratinocyte acantholysis, particularly for the prevention and/or treatment of pemphigus.

Pemphigus is an autoimmune bullous skin condition characterized by loss of keratinocyte adhesion due to autoantibodies directed against desmosomal proteins (desmogleins, dsg). Pemphigus has a world-wide distribution with an incidence of approximately 1-5 per 100,000 per year, and with a female predominance.

Pemphigus is characterized by loss of adhesion of suprabasal keratinocytes that round up in a process known as acantholysis. Pathogenesis of pemphigus is undergoing a major revision, mostly because, in addition to anti-desmoglein antibodies, a new group of anti-cholinergic receptor antibodies can induce acantholysis (Kalish, 2000). Further, it has been demonstrated that steric hindrance alone cannot account for blister formation upon antigen-antibody binding (Kitajima, 2002). Further, it was shown that desmosome formation is not inhibited by pemphigus autoantibodies (PVIgG) binding to pemphigus, while the desmosomal connections are dissociated 24-36 hrs after treatment with PvIgG. During this time, a series of signal transduction steps triggered by PVIgG take place.

These observations suggest a role for apoptosis in pemphigus. Indeed, pemphigus is a disease due to lack of cell adhesion (Payne A S et al, 1978) and apoptosis can occur in association with cell detachment (Marconi et al, lesional pemphigus skin. In particular, acantholytic cells express the major markers of apoptosis (Wang X et al, 2004). More interestingly, TUNEL-labeling nuclei are also found attached to the blister roof, suggesting the presence of apoptotic cells in perilesional skin before detachment. Moreover, apoptotic cells expressing Ig and activated caspase-8 are detected at the edge of the lesion, in areas where no disruption of cell-cell contacts is visible (Wang X et l, 2004). These data definitely demonstrate that in pemphigus, apoptosis takes place in keratinocytes before acantholysis.

Apoptosis plays a fundamental role in the regulation of cellular homeostasis and is involved in many pathophysiologic processes. Apoptosis can follow both cell to cell detachment (Rezgui et al, 2000; Bergin at al, 2000) and loss of cell-matrix interaction (Giancotti and Ruoslahti, 1999).

Fas (or FasR) is a member of the TNF-receptor superfamily which, upon binding with Fas ligand (FasL), triggers apoptosis in many cell systems (Sharma at al, 2000). Intracellular signaling of Fas-FasL-induced apoptosis operates via recruitment of a number of adaptor molecules such as FADD (Fas-associated death domain) and FLICE (FADD-like ICE, caspase 8), which in turn is inhibited by FLIP (FLICE inhibitory protein) (Juo et al, 1998). Fas-FasL interaction is involved in the pathomechanisms of several immune-inflammatory and infectious conditions, such as AIDS (Bahr et al, 1997) and systemic lupus erythematosus (Kovacs at al, 1997). Cutaneous diseases characterized by an implication of Fas-FasL pathway include acute graft versus host disease, toxic epidermal necrolysis and melanoma (Wehrli et al, 2000). Further, it was reported that acantholytic-like lesions are observed in cultured keratinocytes treated with both PVIgG and with anti-FasR, while PvIgG induce the clustering of FasR, FasL and caspase-8 on the cell membrane several hours before the formation of the lesions (Wang X et al, 2004). Moreover, it was reported that the caspase-1-like inhibitor significantly blocked the blister formation in a pemphigus mouse model (Li et al, 2006). Taken together, these data indicate that FasL and the extrinsic apoptotic pathway play a critical role in the mechanisms underlying acantholysis.

Whatever the nature of the pemphigus autoantibodies, exposure to PVIgG up-regulates the expression of several pro-apoptotic genes, including FasL, many hours before acantholysis. Moreover, intravenous IgG (IVIgG) prevents PvIgG-induced up-regulation of FasL and apoptosis in keratinocytes. IVIgG also prevents acantholysis and apoptosis in vivo (Arredondo J et al, 2005).

Without treatment, the mortality of pemphigus vulgaris approaches 100%. Early systemic therapy is required to control pemphigus, but side effects from systemic therapy are a major complication. Treatment includes administration of corticosteroids, medications containing gold, the anti-inflammatory drug dapsone, or medications that suppress the immune system (such as azathioprine, methotrexate, cyclosporin, cyclophosphamide, or mycophenolate mofetil). The most common treatment for pemphigus is nowadays steroids which need to be administered for life and can cause severe side effects. Most pemphigus patients die by these side effects. Some antibiotics are also effective, particularly minocycline and doxycycline. Intravenous immunoglobulin (IVIg) is occasionally used. Plasmapheresis is a process whereby antibody-containing plasma is removed from the blood and replaced with intravenous fluids or donated plasma. Plasmapheresis may be used in addition to the systemic medications to reduce the amount of antibodies in the bloodstream. A number of new molecules are also under development: mycophenolate mofetil, PI-0824, PRTX-100, anti-CD20 are immunesuppressive drugs which act on T and B cells.

The current mortality rate still ranges from 5 to 25%; infection is the most frequent cause of death and long-term immunosuppressive therapy (mainly corticosteroid) is one of the significant factors still provoking a high mortality rate. Immunoglobulin can produce some short-term improvement, but does not seem to induce lasting remissions, and its cost makes it impractical for long-term use.

There are several caveats also in the use of plasmapheresis. Patients suppressed with prednisone or others immunosuppressive agents and receiving plasmapheresis, are at higher risk of sudden death from sepsis. In addition, the treatment is very expensive, and a 2-week hospitalization period is necessary to administer the therapy. Therefore, because of the risk of sudden death from sepsis and the high cost, plasmaphaeresis is indicated only in the most refractory cases where the patient is clearly at risk of dying from the disease itself.

It is an object of the present invention to provide a therapeutic agent for pemphigus. The development of a new drug which blocks FasL would allow to completely prevent cell detachment and the formation of the skin lesion.

In general, the present invention refers to the treatment of a skin disease associated with keratinocyte acantholysis by administering a FasL antagonist. FasL antagonists may be selected from anti FasL antibodies, particularly humanized or human anti FasL antibodies, nucleic acid effector molecules of Fas expression such as antisense molecules or molecules capable of RNA interference such as siRNA molecules, soluble Fas receptor molecules, antagonistic FasL muteins, and low molecular weight chemical compounds inhibiting the Fas-FasL interaction. FasL antagonists prevent keratinocyte apoptosis and subsequent cell-cell detachment (acantholysis). Thus, FasL antagonists are particularly suitable for the prevention and/or treatment of pemphigus, e.g. for the prevention and/or treatment of mucocutaneous pemphigus.

The present invention relates to a medicament containing at least one compound inhibiting the biological effects of FasL. The expression "compound inhibiting the biological effects of FasL" used herein relates to all the compounds which can fully or at least substantially inhibit or neutralize the biological effects of FasL. For example, the inhibitory or neutralizing effect may be based on suppressing the binding of FasL to its natural receptor and therefore the thus caused signal transmissions. This can be achieved e.g. by using antibodies binding to FasL per se or soluble receptors mimicking Fas or antagonistic FasL muteins, thus blocking the binding of FasL to the cellular receptors. Interfering with Fas or FasL expression by siRNA will block Fas/FasL system.

FasL antagonist therapy is either a monotherapy or be given in combination with other medicaments suitable for the treatment of pemphigus or other skin diseases, particularly as described above. For example, a combination therapy of FasL antagonists and steroids might allow a drastic reduction of the steroid doses.

In a preferred embodiment of the present invention, there is provided a therapeutic agent for pemphigus, comprising an antibody against a human Fas ligand, or an active fragment thereof as an active ingredient. The antibody is preferably a chimeric, humanized or human anti-FasL antibody or an antigen-binding fragment or derivative, e.g. a recombinant single chain antibody. If desired, the antibody may be conjugated to effector molecules, e.g. cytostatic, cytotoxic and/or radioactive compounds.

Preferred humanized antibodies suitable for the treatment of skin disease associated with keratinocyte acantholysis, in particular pemphigus according to the present invention, are described in WO 1997/002290A1 ("Anti-Fas ligand antibodies and assay method using the same antibody") or in WO 1998/010070 A1 ("Humanized immunoglobulin reacting specifically with Fas Ligand or active fragments thereof and region inducing apoptosis originating in Fas Ligand humanized antibodies"), the contents of which are herein incorporated by reference. Further preferred human antibodies suitable for the treatment of skin disease associated with keratinocyte acantholysis, in particular pemphigus, according to the present invention, are described in U.S. Pat. No. 7,262,277 ("Antagonistic Anti-hFas ligand human antibodies and fragments thereof"), the content of which is herein incorporated by reference, too. In particular, SEQ ID NO:23 herein corresponds to SEQ ID NO:2 of U.S. Pat. No. 7,262,277 which is the amino acid sequence of the light chain variable region of antibody 3E1 which is produced by hybridoma ATCC PTA-4017; and SEQ ID NO:24 herein corresponds to SEQ ID NO:10 of U.S. Pat. No. 7,262,277, which is the amino acid sequence of the heavy chain variable region of antibody 3E1 which is produced by hybridoma ATCC PTA-4017.

Human or humanized antibodies have at least three potential advantages over mouse and in some cases chimeric antibodies for use in human therapy: 1) because the effector portion is human, it may interact better with the other parts of the human system; 2) the human immune system should not recognize the framework or C region of the humanized antibody as foreign, and therefore the antibody response against such an injected antibody should be less than against a totally foreign mouse antibody or a partially foreign chimeric antibody; 3) injected humanized antibodies will presumably have a half-life more like that of naturally occurring human antibodies, allowing smaller and less frequent doses to be given.

Further preferred FasL antagonists are soluble FasR molecules comprising the extracellular soluble part of the Fas receptor or modified antagonistic FasL molecules which have a competitive or non-competitive antagonistic activity. These molecules inhibit FasL/FasR interactions in that FasL binds to the soluble receptor analogue or the antagonistic FasL molecule binds to the natural receptor thereby reducing or fully eliminating the binding of biologically active FasL to the natural receptor. During treatment with siRNA, an analysis of Fas and/or FasL protein or RNA levels can be used to determine treatment type and the course of therapy in treating a subject. Monitoring of Fas and/or FasL protein or RNA levels can be used to predict treatment outcome and to determine the efficacy of compounds and compositions that modulate the level and/or activity of certain Fas and/or FasL proteins associated with a trait, condition, or disease.

In an especially preferred aspect, the present invention refers to the use of
(i) a monoclonal antibody or an antigen-binding fragment thereof specific for human Fas ligand protein (FasL), wherein said monoclonal antibody comprises at least one heavy chain variable region and at least one light chain variable region, wherein the amino acid sequences of the complementary determining region (CDRs) of the heavy chain are:
($a_1$) CDR H1: Asn Tyr Trp Ile Gly (SEQ ID NO:1),
($b_1$) CDR H2: Tyr Leu Tyr Pro Gly Gly Leu Tyr Thr Asn Tyr Asn Glu Lys Phe Lys Gly (SEQ ID NO:2),
($c_1$) CDR H3: Tyr Arg Asp Tyr Asp Tyr Ala Met Asp Tyr (SEQ ID NO:3) or
($d_1$) a sequence derived by substituting 1, 2 or 3 amino acids of SEQ ID NOs: 1, 2 and/or 3
and/or the amino acid sequences of the complementary determining regions (CDRs) of the light chain are
($a_2$) CDR L1: Lys Ser Thr Lys Ser Leu Leu Asn Ser Asp Gly Phe Thr Thy Leu Gly (SEQ ID NO:4),
($b_2$) CDR L2: Leu Val Ser Asn Arg Phe Ser (SEQ ID NO:5),
($c_2$) CDR L3: Phe Gln Ser Asn Tyr Leu Pro Leu Thr (SEQ ID NO:6) or
($d_2$) a sequence derived by substituting 1, 2 or 3 amino acids of SEQ ID NOs: 4, 5 and/or 6
or
(ii) an antibody or an antigen-binding fragment thereof which recognizes the same epitope on human FasL as the antibody (i),
for the manufacture of a medicament for the prevention and/or treatment of a skin disease associated with keratinocyte acantholysis, particularly of pemphigus.

In a second especially preferred aspect, the present invention refers to the use of
(i) a monoclonal antibody or an antibody-binding fragment thereof specific for human Fas ligand protein (FasL), wherein the monoclonal antibody is produced by the hybridoma cell under Accession No. FERM BP-5045 or an antibody or antibody fragment derived therefrom, or
(ii) a monoclonal antibody or an antigen-binding fragment thereof which recognizes the same epitope of human FasL as the antibody of (i)

for the manufacture of a medicament for the prevention and/or treatment of a skin disease associated with keratinocyte acantholysis, particularly of pemphigus.

In a third especially preferred aspect, the present invention refers to the use of
 (i) a monoclonal antibody or an antigen-binding fragment thereof specific for human Fas ligand protein (FasL), wherein said monoclonal antibody comprises at least one heavy chain variable region and at least one light chain variable region, wherein the amino acid sequences of the complementary determining region (CDRs) of the heavy chain are:
   ($a_1$) CDR H1: Glu Tyr Pro Met His (SEQ ID NO:7),
   ($b_1$) CDR H2: Met Ile Tyr Thr Asp Thr Gly Glu Pro Ser Tyr Ala Glu Glu Phe Lys Gly (SEQ ID NO:8),
   ($c_1$) CDR H3: Phe Tyr Trp Asp Tyr Phe Asp Tyr (SEQ ID NO:9) or
   ($d_1$) a sequence derived by substituting 1, 2 or 3 amino acids of SEQ ID NOs: 7, 8 and/or 9,
and/or the amino acid sequences of the complementary determining regions (CDRs) of the light chain are
   ($a_2$) CDR L1: Arg Ala Ser Gln Asp Ile Ser Asn Tyr Leu Asn (SEQ ID NO:10),
   ($b_2$) CDR L2: Tyr Thr Ser Arg Leu His Ser (SEQ ID NO:11),
   ($c_2$) CDR L3: Gln Gln Gly Ser Thr Leu Pro Trp Thr (SEQ ID NO:12) or
   ($d_2$) a sequence derived by substituting 1, 2 or 3 amino acids of SEQ ID NOs: 10, 11 and/or 12
or
 (ii) an antibody or an antigen-binding fragment thereof which recognizes the same epitope on human FasL as the antibody (i),
for the manufacture of a medicament for the prevention and/or treatment of a skin disease associated with keratinocyte acantholysis, particularly of pemphigus.

In a fourth preferred aspect, the present invention refers to the use of
 (i) a monoclonal antibody or an antibody-binding fragment thereof specific for human Fas ligand protein (FasL), wherein the monoclonal antibody is produced by the hybridoma cell under Accession No. FERM BP-5533, FERM BP-5534 and/or FERM BP-5535 or an antibody or antibody fragment derived therefrom, or
 (ii) a monoclonal antibody or an antigen-binding fragment thereof which recognizes the same epitope of human FasL as the antibody of (i)
for the manufacture of a medicament for the prevention and/or treatment of a skin disease associated with keratinocyte acantholysis, particularly of pemphigus.

In an especially preferred embodiment, the present invention is directed to the use of anti-FasL human antibodies, or antigen-binding portions thereof, comprising a light chain variable region and/or a heavy chain variable region as described in U.S. Pat. No. 7,262,277, the content of which is herein incorporated by reference. In particular, the preferred anti-FasL human antibodies suitable for the treatment of skin disease associated with keratinocyte acantholysis according to the present invention comprise a light chain variable region comprising a polypeptide with the sequence shown in SEQ ID NO 2 of U.S. Pat. No. 7,262,277 (incorporated herein by reference) and further comprising a heavy chain variable region comprising a polypeptide with the sequence shown in SEQ ID NO 10 or 18 of U.S. Pat. No. 7,262,277 (incorporated herein by reference). More particularly, the invention refers to the use of the anti-hFas human antibody 3E1 (produced by the hybridoma cell with accession number ATCC PTA-4017) and/or 4G11 (produced by the hybridoma cell with accession number ATCC PTA-4018) as described in U.S. Pat. No. 7,262,277 (incorporated herein by reference) for the manufacture of a medicament for the prevention and/or treatment of skin disease associated with keratinocyte acantholysis, particularly of pemphigus.

In a still further preferred aspect, the present invention refers to the use of
 (i) a monoclonal human antibody or an antigen-binding fragment thereof specific for human Fas ligand protein (FasL), wherein said monoclonal antibody comprises at least one heavy chain variable region and at least one light chain variable region, wherein the amino acid sequences of the complementary determining regions (CDRs) of the heavy chain are:

```
                                            (SEQ ID NO: 13)
($a_1$) CDR H1: Arg His Gly Ile Thr
or
                                            (SEQ ID NO: 14)
($a_2$) CDR H1: Ser His Gly Ile Ser,
                                            (SEQ ID NO: 15)
($b_1$) CDR H2: Trp Ile Asn Ala Tyr Asn Gly Asn Thr

Asn Tyr Ala Gln Lys Val Gln Gly
or
                                            (SEQ ID NO: 16)
($b_2$) CDR H2: Trp Ile Asn Ala Tyr Ser Gly Asn Thr

Asn Tyr Ala Gln Lys Leu Gln Gly,
                                            (SEQ ID NO: 17)
($c_1$) CDR H3: Glu Thr Met Val Arg Gly Val Pro Leu

Asp Tyr
or
                                            (SEQ ID NO: 18)
($c_2$) CDR H3: Glu Thr Met Val Arg Gly Val Pro Cys

Asp Tyr
or ($d_1$) a sequence derived by substituting 1, 2 or 3 amino acids of SEQ ID NOs 13, 14, 15, 16, 17 and/or 18,
``` and/or the amino acid sequences of the complementary determining regions (CDRs) of the light chain are

```
                                            (SEQ ID NO: 19)
($a_3$) CDR L1: Arg Ala Ser Gln Ser Val Ser Ser Ser

Tyr Leu Ala,
                                            (SEQ ID NO: 20)
($b_3$) CDR L2: Gly Ala Ser Ser Arg Ala Thr,
                                            (SEQ ID NO: 21)
($c_3$) CDR L3: Gln Gln Tyr Gly Ser Ser Pro Trp Thr
or ($d_3$) a sequence derived by substituting 1, 2 or 3 amino acids of SEQ ID NOs: 19, 20 and/or 21
``` or
 (ii) an antibody or an antigen-binding fragment thereof which recognizes the same epitope on human FasL as the antibody (i), for the manufacture of a medicament for the prevention and/or treatment of a skin disease associated with keratinocyte acantholysis, particularly of pemphigus.

In a finally further preferred aspect, the present invention refers to the use of
(i) a monoclonal antibody or an antigen-binding fragment thereof specific for human Fas ligand protein (FasL), wherein the monoclonal antibody is produced by the hybridoma cell under Accession No. ATCC PTA-4017 and/or ATCC PTA-4018 or an antibody or antibody fragment derived therefrom, or
(ii) a monoclonal antibody or an antigen-binding fragment thereof which recognizes the same epitope of human FasL as the antibody of (i)
for the manufacture of a medicament for the prevention and/or treatment of a skin disease associated with keratinocyte acantholysis, particularly of pemphigus.

The hybridoma cell under Accession No. ATCC PTA-4017 and ATCC PTA-4018 have been deposited on 29 Jan. 2002 with the American Type Culture Collection, 10801 University Boulevard, Manassas, Va. 20110-2209 (USA).

The medicament of the present invention may be provided as a pharmaceutical composition together with a pharmaceutically acceptable carrier. Preferably, the pharmaceutical composition is administered by injection or infusion, e.g. intravenously, intraarterially, subcutaneously, intraperitoneally or by other suitable means. The composition may be administered locally or systemically. Preferably, the composition is administered systemically.

Pharmaceutical compositions suitable for use in the invention comprise the active agent in an effective amount to achieve the intended purpose. An effective dose of a medicament of the present invention may be in the range of 0.1 μg to 100 mg, up to a total dose of about 1 g depending upon the route of administration. The pharmaceutical compositions may be administered daily, e.g. once or several times, or every two to four days, every week or once in two weeks. The medicament may be administered in a single treatment cycle consisting of one or several medicament administrations or in several treatment cycles each consisting of one or several medicament administrations. Each treatment cycle may have a duration of one day up to several weeks, months, or even years.

Hence, according to the present invention the medicament may also be used in a combination therapy with at least one further therapy effective against a skin disease associated with keratinocyte acantholysis and in particular against pemphigus. The medicament will be used either alone or in combination with other immunosuppressive drugs, particularly with steroids, in order to reduce their dose and/or to minimize their chronic side effects. When used in combination, the medicament will preferably be administered on a monthly basis. When used alone, the medicament will preferably be administered continuously within a time frame depending on the individual case.

Further, the present invention shall be explained in more detail by the following examples.

BRIEF DESCRIPTION OF THE DRAWINGS

FIGS. 4A and 4B show measurement of FasL levels in sera from pemphigus patients by a two-site enzyme immunoassay (ELISA). Serum concentration was determined by absorbance at 450 nm against recombinant human FasL standard protein.

EXAMPLES

Figure 1:
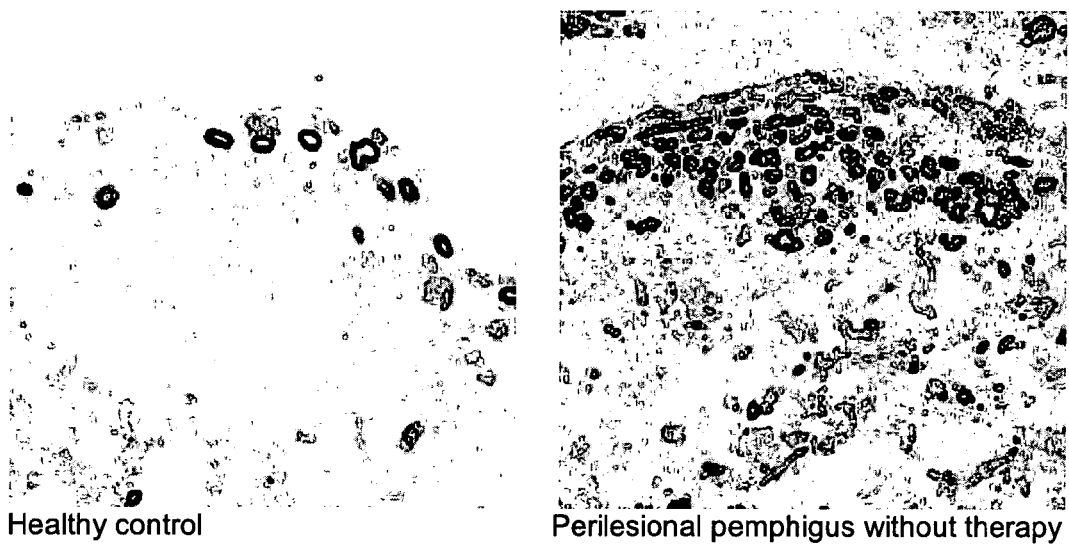
FIG. 1 shows results of an evaluation of the presence of apoptosis in epidermis from perilesional skin in frozen sections from untreated pemphigus patients by TUNEL staining.

We first evaluated the presence of apoptosis in epidermis from perilesional skin in frozen sections from untreated pemphigus patients by TUNEL staining. Fluorescent specimens were analyzed by confocal scanning laser microscopy. In suprabasal layers from perilesional epidermis most keratinocytes are apoptotic, as compared to normal skin (FIG. 1).

Figure 2:
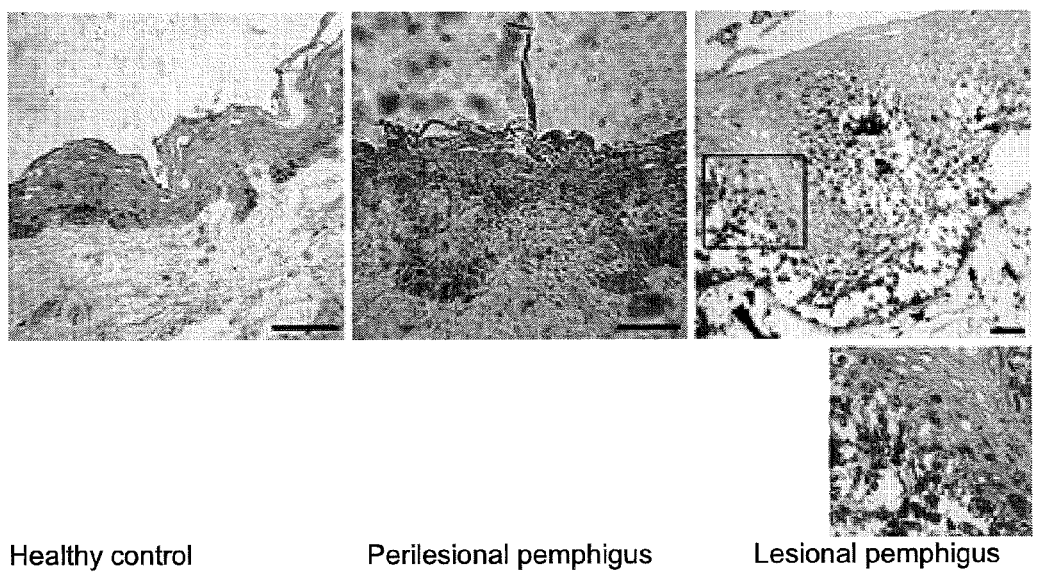
FIG. 2 shows results of an evaluation of apoptosis in pemphigus lesions using formalin-fixed and paraffin embedded biopsies and detected the active form of caspase-3. Staining protocol was performed by UltraVision LP Detection System AP Polymer and Fast Red Chromogen.

In order to confirm apoptosis in pemphigus lesions we used formalin-fixed and paraffin embedded biopsies and detected the active form of caspase-3. Staining protocol was performed by UltraVision LP Detection System AP Polymer and Fast Red Chromogen (Lab Vision Corporation, Calif., USA) according to manufacturer's instruction. Visualization was obtained with Fast Red tablets in naphthol phosphate substrate. In pemphigus samples we found that caspase-3 fragment is located both in the roof and in the floor of the blister, with some cells being positive in perilesional epidermis (FIG. 2). This result seems to indicate that keratinocyte cell death occurs before the detachment of keratinocytes leading to acantholysis.

Figure 3:
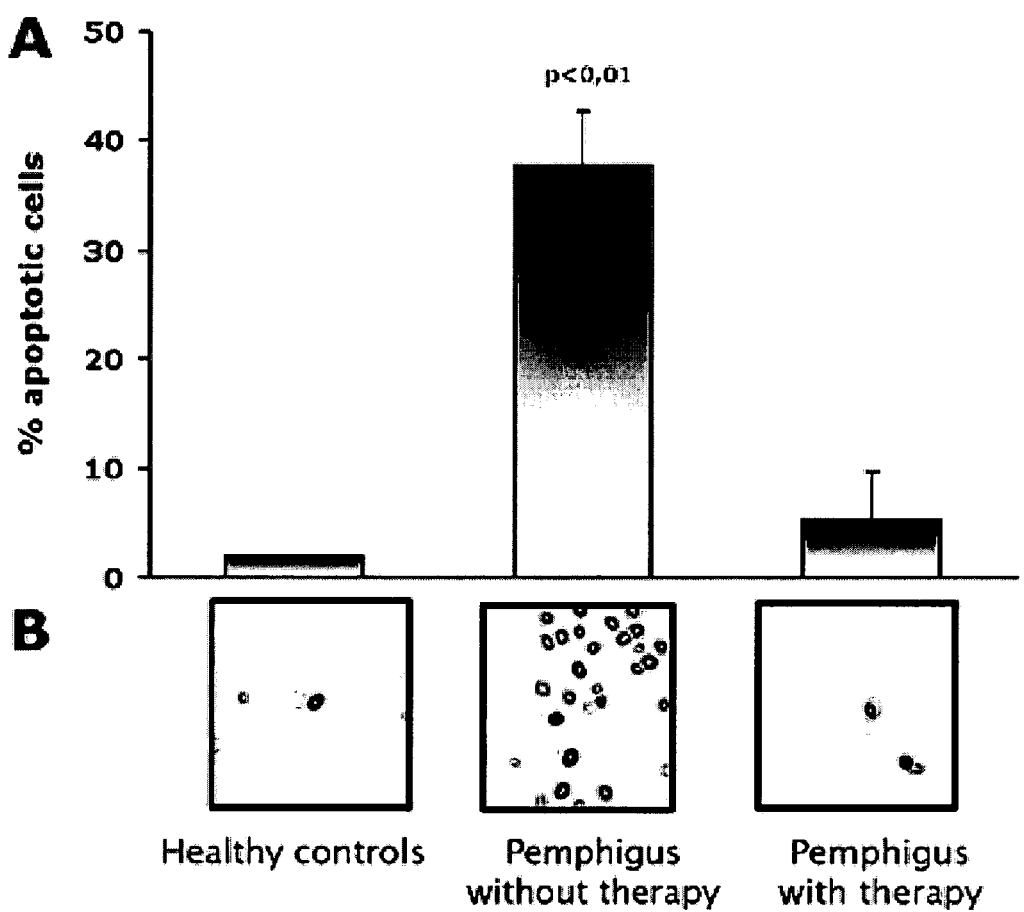
FIGS. 3A and 3B show results of evaluation of whether pemphigus sera are capable of inducing apoptosis in normal human keratinocytes. Apoptosis was evaluated by TUNEL staining in situ.

As apoptotic keratinocytes are abundantly expressed in pemphigus, we wanted to explore whether pemphigus sera are capable of inducing apoptosis in normal human keratinocytes. To this purpose, keratinocytes were plated in chamber slides and cultured in serum-free medium (KGM) up to preconfluence. Cells were then cultured in keratinocyte basal medium and treated for 48 h with the addition of 25% serum from either untreated patients or patients treated with systemic corticosteroids. Sera from healthy subjects were used as controls. Apoptosis was evaluated by TUNEL staining in situ. Approximately 100 cells were evaluated, in randomly selected fields, and the percentage of TUNEL-positive cells was counted. Sera from pemphigus but not from healthy subjects or patients undergoing steroid treatment induced apoptosis in human keratinocytes (FIG. 3 A-B).

As the Fas/FasL system is implicated in many apoptotic processes also at the skin level (Wehrli et al, 2000), we measured FasL levels in sera from pemphigus patients by a two-site enzyme immunoassay (ELISA). Serum concentration was determined by absorbance at 450 nm against recombinant human FasL standard protein. FasL levels were very high in sera from untreated patients and below the limit of detection in sera from patients treated with corticosteroids or in sera from healthy subjects. Sera from HBV patients were used as positive control (FIG. 4A). In one patient, FasL levels progressively decreased with systemic steroid therapy (FIG. 4B).

Figure 5:
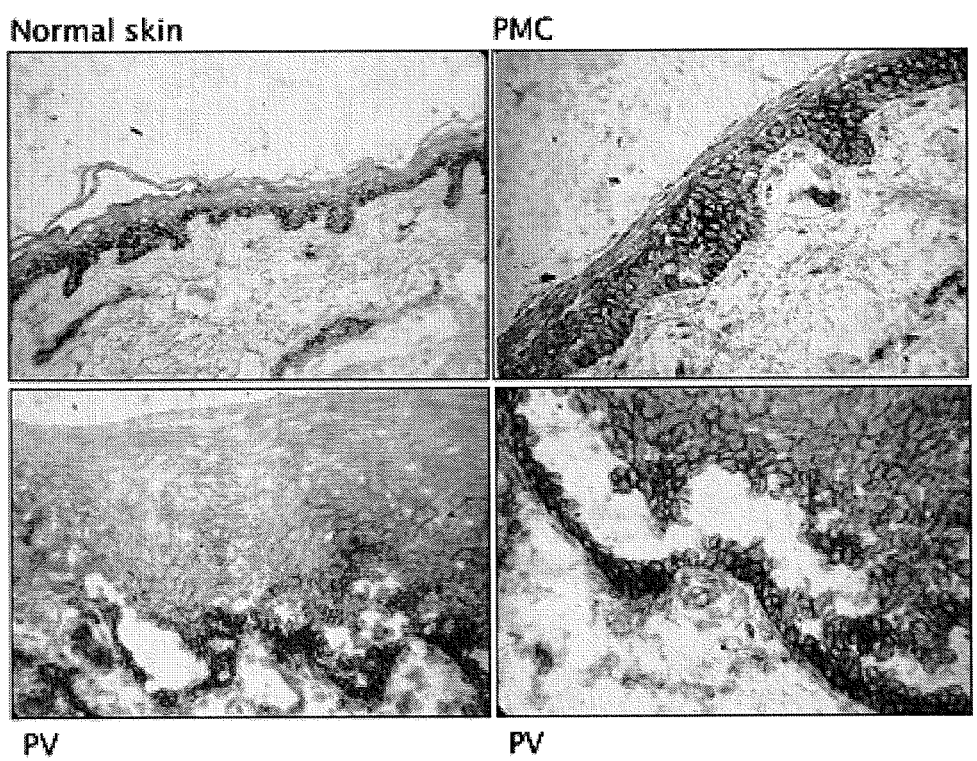
FIG. 5 shows results from expression of the FasL cognate receptor FasR by use of formalin-fixed and paraffin embedded biopsies.

As FasL is contained in high amounts in pemphigus sera, we looked at the expression of its cognate receptor FasR. To this purpose we used formalin-fixed and paraffin embedded biopsies. Staining protocol was performed by UltraVision LP Detection System AP Polymer and Fast Red Chromogen (Lab Vision Corporation, Calif., USA) according to manufacturer's instruction. Visualization was obtained with Fast Red tablets in naphthol phosphate substrate. While FasR is expressed only in basal keratinocytes in normal skin, in active pemphigus lesions, FasR is detected both in the basal and in the suprabasal cells. Even more intriguing, in mucocutaneous pemphigus (PMC) FasR seems to be expressed throughout the epidermal layers and even before blister formation (FIG. 5).

FasL is one of the major triggers of the caspase-8 activated extrinsic apoptotic pathway. Therefore, we wanted to evaluate whether this pathway plays a role in pemphigus apoptosis. To this purpose, patient sera were pretreated with anti-FasL neutralizing antibody or caspase-8 inhibitor, and added to keratinocyte cultures. Keratinocytes were cultured in KGM and treated with pemphigus sera or with sera from untreated patients. Sera were pretreated with anti-FasL neutralizing antibody (2.5 mg per ml for 30 min) or caspase-8 inhibitor Z-IETD-FMK (100 µM for 30 min). Apoptosis was evaluated by TUNEL staining. Addition of anti-FasL neutralizing antibody or caspase-8 inhibitor partially prevented pemphigus sera-induced keratinocyte apoptosis (FIG. 6).

Figure 6:
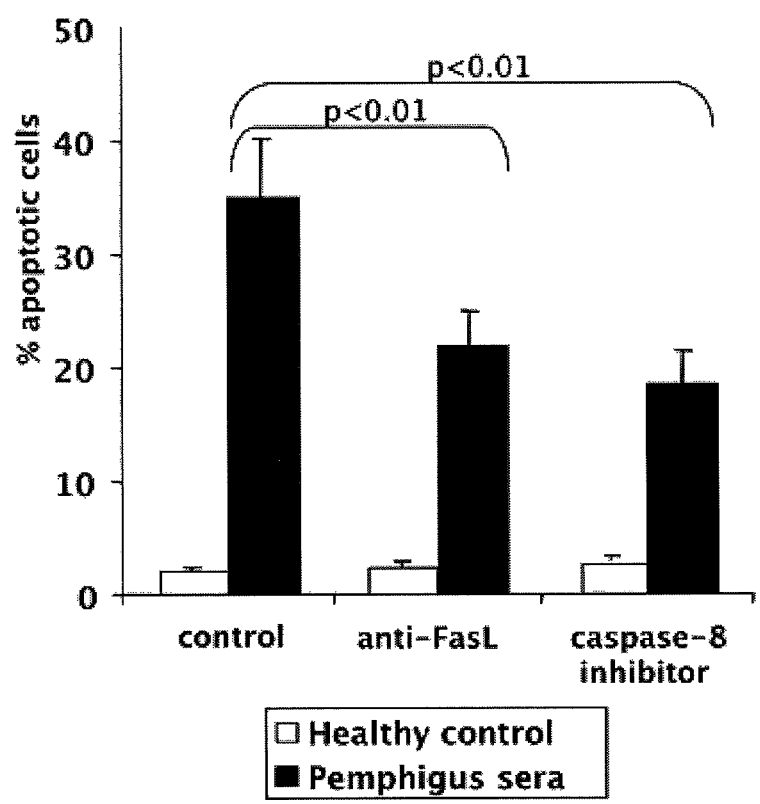
FIG. 6 shows the effect of untreated pemphigus sera on apoptosis in presence of either anti-FasL neutralizing antibody or capase-8 inhibitor in vitro. Apoptosis was evaluated by TUNEL staining in situ.
Figure 7:
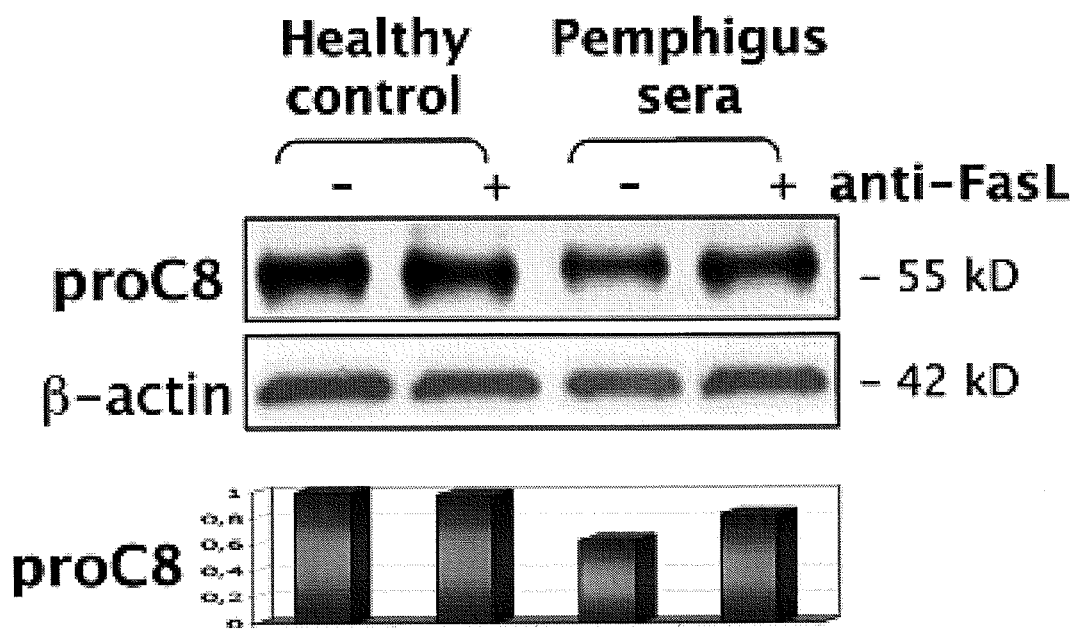
FIG. 7 shows evaluation of keratinocytes treated as in FIG. 6 and provided with either anti-FasL antibody or irrelevant immunoglobulins with the cells then homogenized in RIPA buffer for Western blotting analysis and membranes incubated with anti human caspase-8 or anti-b-actin antibodies. The relative intensity of bands on autoradiograms was quantified by scanning laser densitometry.

In addition, Keratinocytes were treated as in FIG. 6 and provided with either anti-FasL antibody or irrelevant immunoglobulins. Cells were then homogenized in RIPA buffer for Western blotting analysis. Membranes were incubated with anti human caspase-8 or anti-b-actin antibodies. The relative intensity of bands on autoradiograms was quantified by scanning laser densitometry. The results shown that caspase-8 was markedly activated in keratinocytes treated with pemphigus sera, as compared to untreated cells, while caspase cleavage was partially inhibited by pre-treatment with anti-FasL antibody (FIG. 7).

Taken together, these data suggest that pemphigus sera induce keratinocyte apoptosis through the extrinsic apoptotic pathway triggered by the Fas/FasL system.

Figure 8:
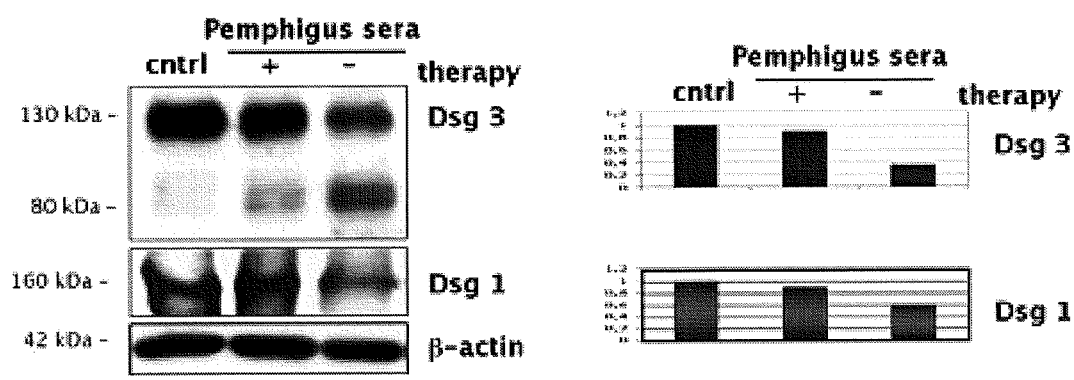
FIG. 8 shows the effect of pemphigus sera on desmoglein degradation in presence or in absence of steroid therapy. Protein extracts from keratinocyte treated cultures were analysed by Western blotting using anti-Dsg3 and anti-Dsg1 antibodies.

Recent studies have shown that components of the cadherin-catenin adhesion complex in epithelial adherens junctions are targeted by caspases during apoptosis (Weiske et al, 2001). In order to evaluate whether Fas/FasL-induced apoptotic pathway is also responsible for desmosomal separation, we treated for 72 hrs confluent keratinocytes, cultivated in KGM in presence of 1.8 mM $CaCl_2$, with pemphigus sera with or without therapy. Protein extracts from the culture were analyzed by Western blotting using anti-Dsg1 and anti-Dsg3 antibodies. β-actin was used as internal control. We found that pemphigus sera can cleave Dsg1 and Dsg3. In particular, sera from untreated patients, but not from patients under steroid therapy strikingly cleave Dsg1 and Dsg3. (FIG. 8).

Figure 9:
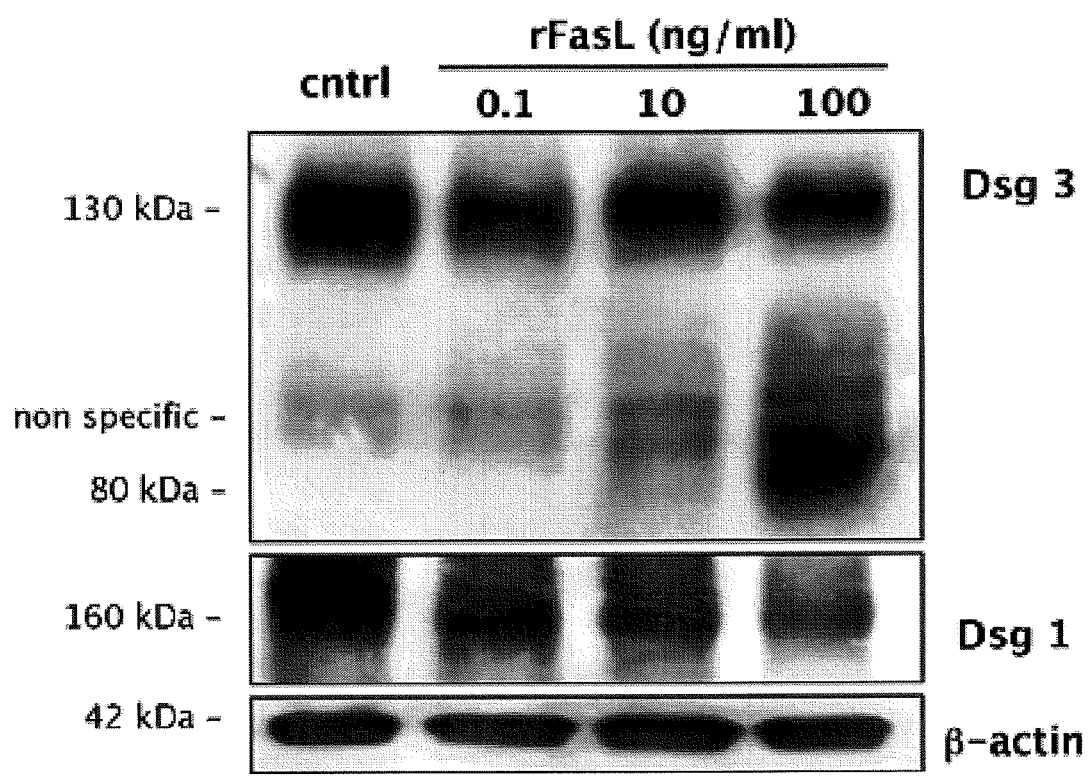
FIG. 9 shows results after treatment of keratinocytes with increasing amounts of FasL. Protein extracts from the culture were analyzed by Western blotting using anti-Dsg1 and anti-Dsg3 antibodies.

Most importantly, treatment of keratinocytes with increasing amounts of FasL (0.1, 10, 100 ng/ml) for 72 hrs, cleaved dsgs in a dose-dependent manner. Protein extracts from the culture were analyzed by Western blotting using anti-Dsg1 and anti-Dsg3 antibodies. β-actin was used as internal control. These doses are consistent with the ones detected in pemphigus sera (FIG. 9).

Figure 10:
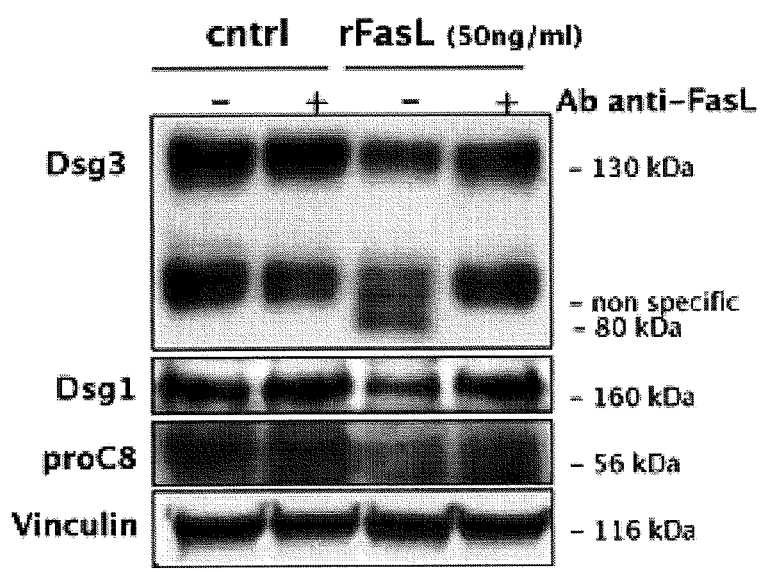
FIGS. 10A and 10B show that an anti-FasL antibody prevents FasL-induced dsg cleavage, inhibits caspase-8-induced apoptosis and prevents FasL-induced cell-to-cell detachment.
Figure 10:
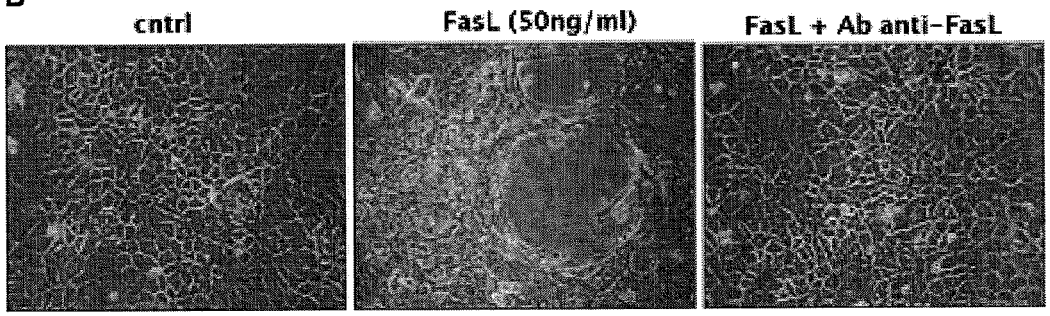

Given that FasL exerts an important role in the pathogenesis of pemphigus, we have tested an anti-FasL antibody (NOK2, antibody produced by the hybridoma cell line NOK2, accession number No. FERM BP-5045). Confluent keratinocytes, cultivated in KGM with 1.8 mM $CaCl_2$, were treated for 72 hrs with: 1. KGM alone; 2. anti-FasL (NOK2, 15 µg/ml) Ab; 3. FasL (50 ng/ml); 4. FasL+anti-FasL Ab. We present evidence that anti-FasL Ab (NOK2) prevents FasL-induced dsg cleavage. We also show that anti-FasL Ab (NOK2) inhibits caspase-8-induced apoptosis (FIG. 10 A). FIG. 10B shows that anti-FasL (NOK2) Ab prevents FasL-induced cell-to-cell detachment, i.e. acantholysis.

Figure 11:
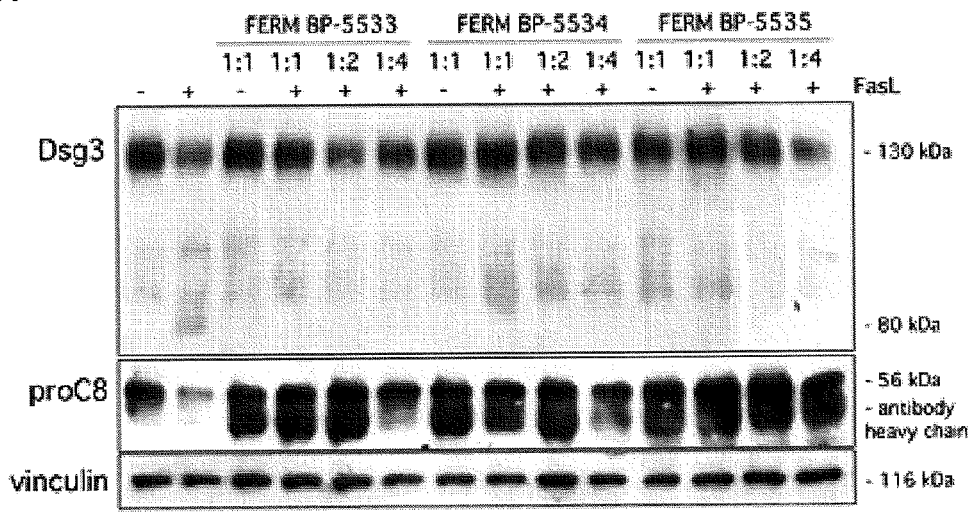
FIGS. 11A, 11B and 11C show that different anti-FasL antibodies prevent FasL-induced dsg cleavage, inhibit caspase-8-induced apoptosis and block FasL-induced cell-to-cell detachment.
Figure 11:
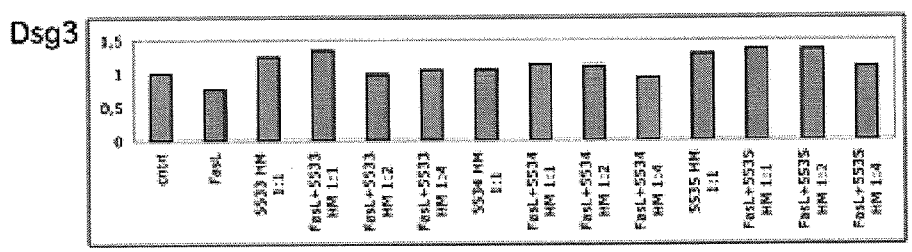
Figure 11:
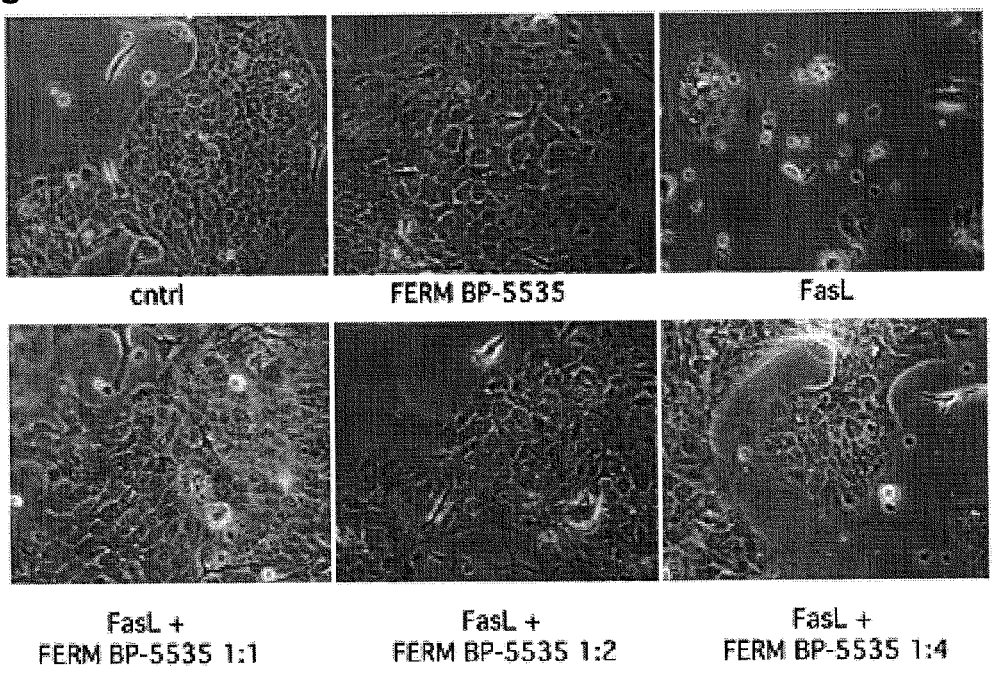

In order to further confirm the central role of FasL, we have used other anti-FasL antibodies (F918-7-3, antibody produced by the hybridoma cell line with accession number No. FERM BP-5533; F918-7-4, antibody produced by the hybridoma cell line with accession number No. FERM BP-5534; F919-9-18, antibody produced by the hybridoma cell line with accession number No. FERM BP-5535). Confluent keratinocytes, cultivated in KGM with 1.8 mM $CaCl_2$, were treated for 72 his with: KGM alone; recombinant FasL (50 ng/ml); hybridoma medium diluted 1:1 in KGM; FasL+hybridoma medium at different dilution in KGM. We present evidence that anti-FasL antibodies prevents FasL-induced dsg3 cleavage in a dose-dependent manner (FIG. 11A and FIG. 11B), inhibiting caspase-8 induced apoptosis activation (FIG. 11A). FIG. 11C shows that the FasL Ab contained in the medium from hybridoma cell line FERM BP-5535 prevents FasL-induced cell-to-cell detachment, i.e. acantholysis.

Figure 12:
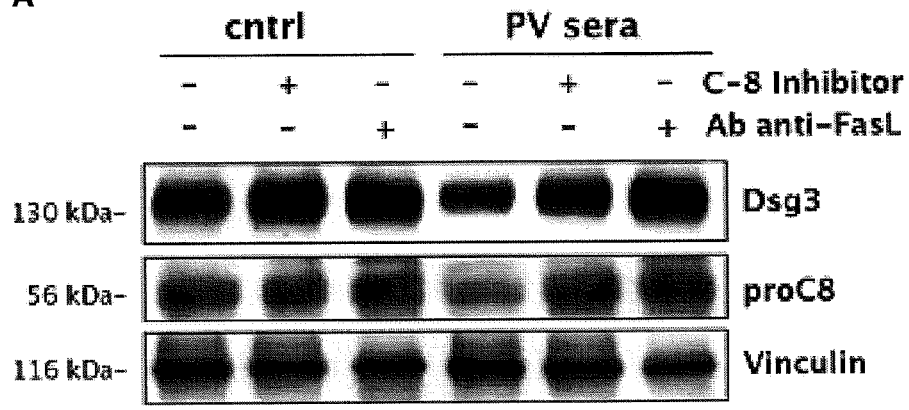
FIGS. 12A and 12B show the effect of untreated pemphigus sera on dsg cleavage, caspase-8 activation and acantholysis in presence of either anti-FasL neutralizing antibody or capase-8 inhibitor in vitro.
Figure 12:
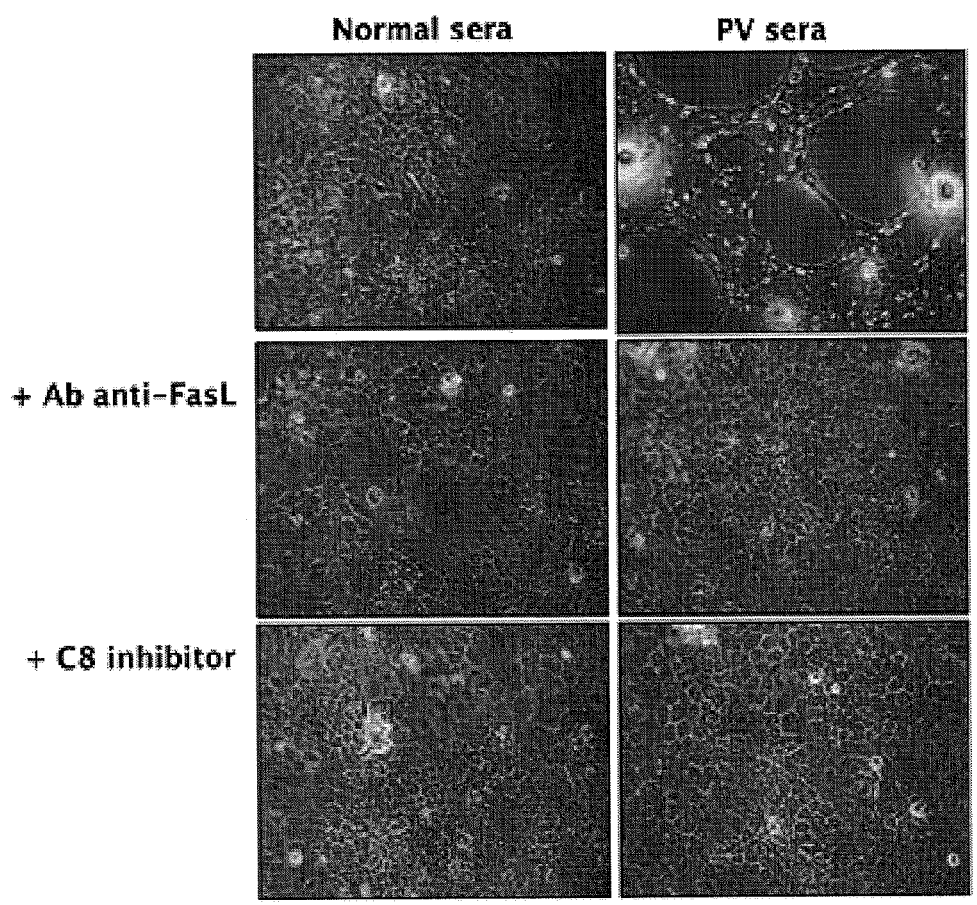

To investigate whether the extrinsic apoptotic pathway is responsible for dsg cleavage, we pretreated confluent keratinocytes with caspase-8 inhibitor Z-IETD-FMK (100 µM for 30 min) or with anti-FasL (NOK2, 15 µg/ml)Ab. Then cells were incubated for 72 hrs with healthy or untreated pemphigus sera. Protein extracts from the culture were analyzed by Western blotting using anti-Dsg3 antibodies and anti-caspase-8 Ab. Vinculin was used as internal control. (FIG. 12A). FIG. 12B shows that cell detachment (i.e. acantholysis) is prevented by anti-FasL Ab or caspase-8 inhibitor. These results indicate that inhibiting FasL or the caspase-8-activated apoptotic pathway prevents both caspase-8 activation and dsg cleavage, thus blocking acantholysis.

Figure 13:
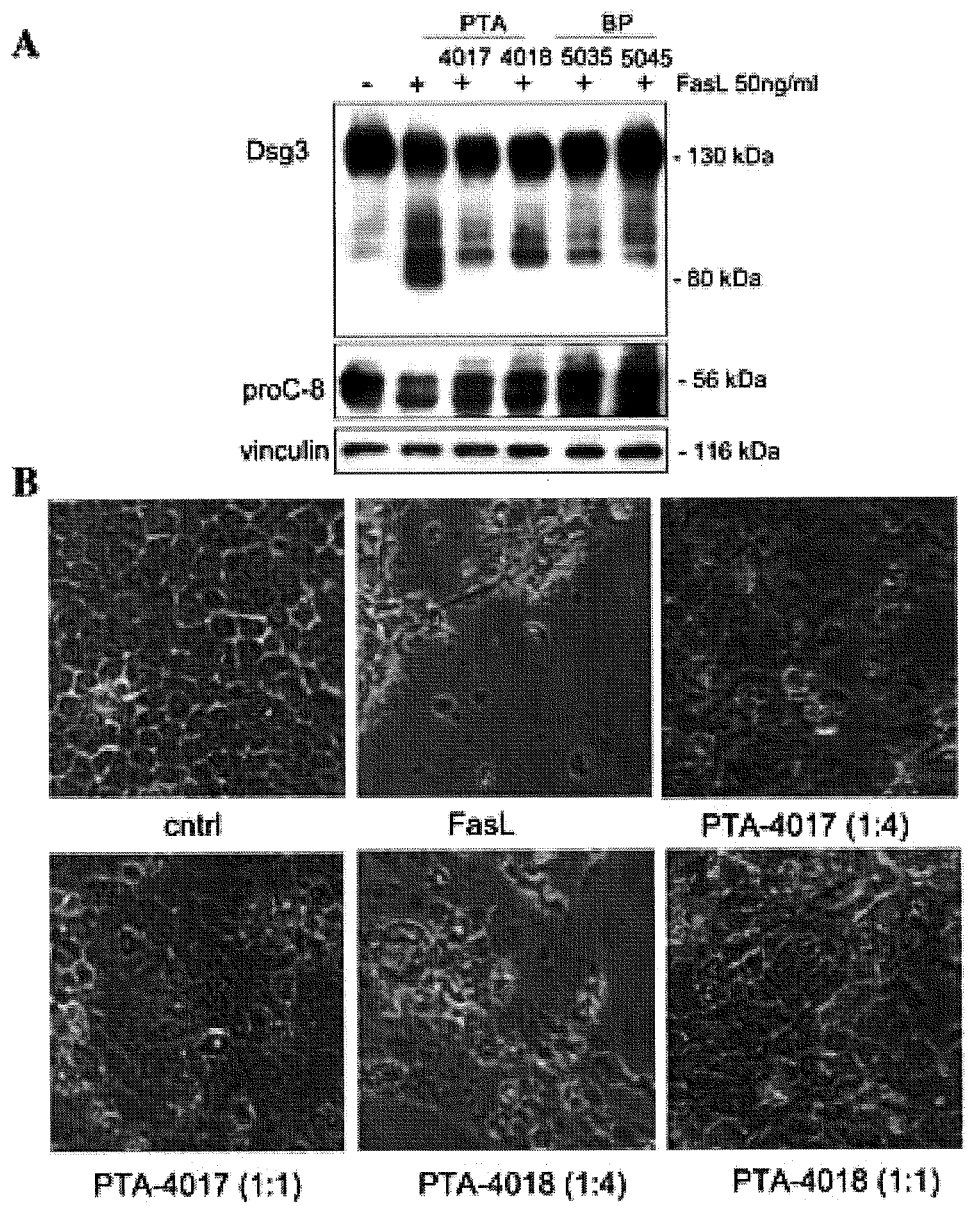
FIGS. 13A and 13B show that actual human antibodies as well as the humanized antibodies prevent cleaving Dsg3 and activate caspase-8 and that different concentrations of the human anti-FasL antibodies prevent cell-to-cell detachment and acantholysis.

In order to evaluate also the role of human anti-FasL antibodies (human antibody 3E1, produced by the hybridoma cell line with accession number No. ATCC PTA-4017 (antibody PTA-4017) and human antibody 4G11, produced by the hybridoma cell line with accession number No. ATCC PTA-4018 (antibody PTA-4018)), human keratinocytes were cultivated in KGM (1.8 nM CaCl2) and treated with recombinant FasL (50 ng/ml) alone or in combination with the PTA-4017 and PTA-4018 antibodies at different dilutions. Anti-FasL humanized antibodies BP-5035 and BP-5045 already tested in FIGS. 10 to 12 were used as controls. FIG. 13A shows that while FasL alone cleaves Dsg3 and activates caspase-8, both the human antibodies PTA-4017 and PTA-4018 and the humanized antibodies BP-5035 and BP-5045 prevent this effect (western blotting). FIG. 13B demonstrates that while FasL alone induces cell-to-cell detachment and acantholysis, different concentrations of the human anti-FasL antibody PTA-4017 and PTA-4018 prevent this effect.

In conclusion we have shown that FasL exert dual activity, by both activating the caspase-8 mediated extrinsic apoptotic pathway and Dsg cleavage. In agreement with our work, Wang and coworkers (Wang et al, 2004) have suggested that apoptosis could be the cause of the acantholytic phenomenon. They showed that PV-IgG and an antibody against Fas receptor (anti-FasR) induce lesions in vitro in a similar way, causing: (1) secretion of soluble FasL; (2) elevated cellular amounts of FasR, FasL (soluble and membranal), Bax and p53 proteins; (3) reduction in levels of cellular Bcl-2; (4) enrichment in caspase 8, and activation of caspases 1 and 3; (5) coaggregation of FasL and FasR with caspase 8 in membranal death-inducing signaling complex (DISC). Hence, the Fas-mediated death signaling pathway seems to be involved in lesion formation.

A well established animal model has been long and widely used for studying pemphigus. Passive transfer of PVIgG into neonatal mice induce cell detachment and the formation of the bulla. This model has been used to assess the involvement of apoptosis and FasL in the pathogenesis of pemphigus. We injected subcutaneously PVIgG (5 mg/g/BW) purified from patients sera in newborn C57BL/6N CrI mice. Normal newborn mice treated with IgG purified from sera of healthy individuals (NIgG) will be used as controls. Animals were sacrificed 20 hours after injection.

Figure 14:
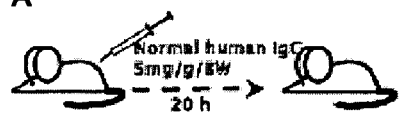
FIG. 14 shows results from hematoxilin and eosin staining in sections from mice treated with PVIgG or normal human IgG to demonstrate blister development and apoptosis activation (TUNEL and active caspase-3).
Figure 14:
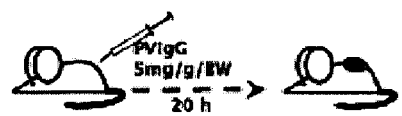
Figure 14:
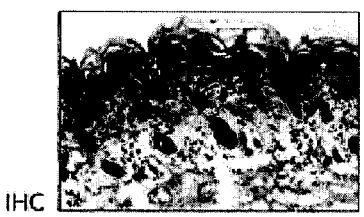
Figure 14:
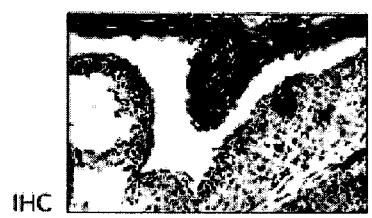
Figure 14:
Figure 14:
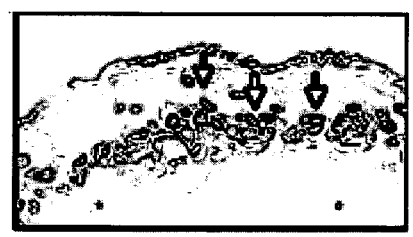
Figure 14:
Figure 14:
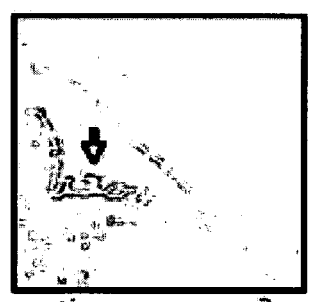

Hematoxilin and eosin staining shows that blister develop only in mice treated with PVIgG, but not in mice treated with normal human IgG (FIG. 14 A). Apoptosis was detected either by TUNEL or by caspase-3 activation only in mice treated with PVIgG (FIG. 14B).

Figure 15:
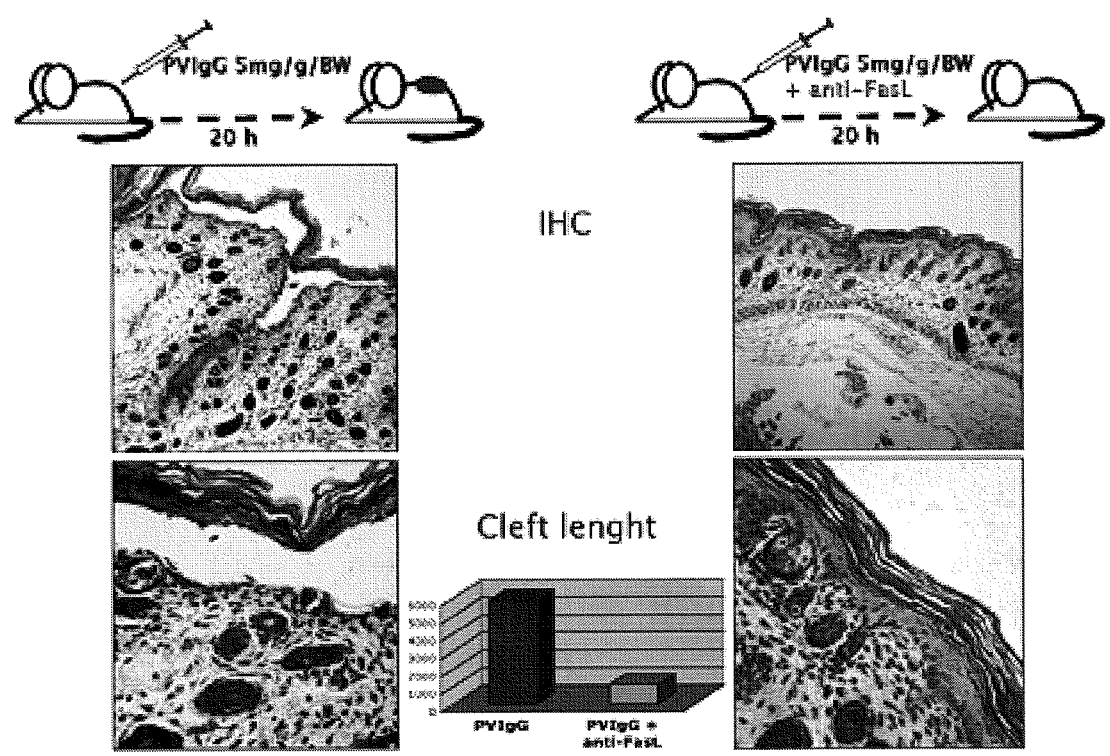
FIG. 15 shows effect by H & E staining on mice administered PVIgG or PVIgG plus anti-FasL antibody.

In order to evaluate the role of FasL in vivo, mice were treated with PVIgG or PVIgG plus anti-FasL antibody (MFL3 clone, specific for mouse). Anti-FasL (40 µg/mouse) was administered 3 hrs after PVIgG injection and prevented blister formation in mice, as shown by H & E staining. In addition, the length of clefts in anti-FasL treated mice was markedly reduced (FIG. 15).

In conclusion we have shown that FasL exert dual activity, by both activating the caspase-8-mediated extrinsic apoptotic pathway and Dsg cleavage. Most importantly, blocking FasL protects from acantholysis in vitro and in vivo.

REFERENCES

Aoudjit F and Vuori K: Matrix attachment regulates FAS-induced apoptosis in endothelial cells: a role for c-FLIP and implications for anoikis. *J Cell Biol* 152: 633-643, 2001

Arredondo J et al Am J Pathol 167:1531-1544, 2005

Bahr G M, Capron A, Dewulf J, Nagata S, Tanaka M, Bourez J M, Mouton Y. Elevated serum level of Fas ligand correlates with the asymptomatic stage of human immunodeficiency virus infection. *Blood* 90:896-898, 1997

Bergin E, Levine J S, Koh J S, Lieberthal W: Mouse proximal tubular cell-cell adhesion inhibits apoptosis by a cadherin-dependent mechanism. *Am J Physiol Renal Physiol* 278: F758-F768, 2000

Du, Z., et al., Biochem. Biophys. Res. Commun., 1996 226, 595-600

Frisch S M: Evidence for a function of death-receptor-related, death-domain-containing proteins in anoikis. *Current Biol* 9:1047-1049, 1999

Frisch S M, Francis H: Disruption of epithelial cell-matrix interactions induces apoptosis. *J Cell Biol* 124:619-626, 1994

Frisch S M, Screaton R A: Anoikis mechanisms. *Curr Opin Cell Biol* 13:555-562, 2001

Giancotti F G, Ruoslahti E Integrin signaling. *Science* 285: 1028-1032, 1999

Gniadecki R, Jemec G B E, Thomsen B M, Hansen M: Relationship between keratinocyte adhesion and death: anoikis in acantholytic diseases. *Arch Dermatol Res* 290:528-532, 1998

Grossman J, Walther K, Artinger M, Kiessling S, Scholmerich J: Apoptotic signaling during initiation of detachment-induced apoptosis ("anoikis") of primary human intestinal epithelial cells. *Cell Growth & Diff* 12:147-155, 2001

Jolles S, Hughes J, Whittaker S: Dermatological uses of high-dose intravenous immunoglobulin. *Arch Dermatol* 134:80-86, 1998

Juo P, Kuo C J, Yuan J, Blenis J: Essential requirement for caspase-8/FLICE in the initiation of the Fas-induced apoptotic cascade. *Curr Biol* 8:1001-1008, 1998

Kalish R S: pemphigus vulgaris: the other half of the story. *J Clin Invest* 106: 1433-1435, 2000

Kitajima Y: Mechanisms of desmosome assembly and disassembly. Clin Exp Dermatol. 27:684-90, 2002

Kovacs B, Liossis S N, Dennis G J, Tsokos G C: Increased expression of functional Fas ligand in activated T-cells from patients with systemic lupus erythematosus. *Autoimmunity* 25:213-221, 1997

Lee, J., et al. Endocrinology, 1997, 138, 2081-2088

Li N, Zhao M, Liu Z, Diaz L A: Pathogenic role of apoptosis in experimental pemphigus. *J Invest Dermatol* 126: 173 Abstract, 2006

Marconi A, Atzei P, Panza C, Ella C, Tiberlo R, Truzzi F, Wachter T, Leverkus M, Pincelli C: FLICE/caspase-8 activation triggers anoikis induced by $\beta_1$ integrin blockade in human keratinocytes. J Cell Sci 117: 5815-5823, 2004

Marconi A, Vaschieri C, Zanoli S, Giannetti A, Pincelli C Nerve growth factor protects human keratinocytes from ultraviolet-B-induced apoptosis. *J Invest Dermatol* 113: 920-927, 1999

Nishimura S, Adachi M, Ishida T, Matsunaga T, Uchida H, Hamada H, Imai K: Adenovirus-mediated transfection of caspase-8 augments anoikis and inhibits peritoneal dissemination of human gastric carcinoma cells. *Cancer Res* 61:7009-7014, 2001

O'Connell, J., et al. J. Exp. Med., 184, 1075-1082, 1996

Payne A S Curr Opin Cell Biol 16: 536-543, 2004

Pincelli C, Haake A R, Benassi L, Grassilli E, Magnoni C, Ottani D, Polakowska R, Franceschi C, Giannetti A Autocrine nerve growth factor protects human keratinocytes from apoptosis through its high affinity receptor (trk): a role for bcl-2. *J Invest Dermatol* 109: 757-764, 1997

Queen et al., Proc. Natl. Acad. Sci. USA 86 (1989), 10029, and Verhoeyan et al., Science 239 (1988), 1534

Reed J C: Mechanisms of apoptosis. *Am J Pathol* 157:1415-1430

Rezgui S S, Honore S, Rognoni J-B, Martin P-M, Penel C: Up-regulation of α2β1 integrin cell-surface expression protects A431 cells from epidermal growth factor-induced apoptosis. *Int J Cancer* 87: 360-367, 2000

Rytomaa M, Martins L M, Downward J: Involvement of FADD and caspase-8 signalling in detachment-induced apoptosis. *Current Biol* 9:1043-1046, 1999

Sharma K, Wang R X, Zhang L Y, Yin D L, Luo X Y, Solomon J C, Jiang R F, Markos K, Davidson W, Scott D W, Shi Y F: Death the Fas way: regulation and pathophysiology of Fas and its ligand. *Pharmacol Thor.* 88:333-347, 2000

Tiberio R, Marconi A, Fila C, Fumelli C, Pignatti M, Krajewski S, Giannetti A, Reed J C, Pincelli C: Keratinocytes enriched for stem cells are protected from anoikis via an integrin signaling pathway, in a Bcl-2 dependent manner. *FEBS Letters* 26318:1-6, 2002

Turley, J. M., et al. Cancer Res., 1997, 57, 881-890

Viard I, Wehrli P, Bullani R, Schneider P, Holler N, Salomon D, Hunzinker T, Saurat J-H, Tschopp J, French L: Inhibition of toxic epidermal necrolysis by blockade of Fas with human intravenous immunoglobulin. *Science* 282:490-493, 1998

Wang X. et al: Possible apoptotic mechanism in epidermal cell acantholysis induced by pemphigus vulgaris autoimmunoglobulins *Apoptosis* 2004; 9: 131-143

Wehrli P, Viard I, Bullani R, Tschopp J, French L E. Death receptors in cutaneous biology and disease. *J Invest Dermatol* 115:141-148, 2000

Weiske J, Schoneberg T, Schroder W, Hatzfeld M, Tauber R, Huber O: The fate of desmosomal proteins in apoptotic cells. *J Biol Chem* 276:41175-41181, 2001

Yang, Y., et al., J. Exp. Med., 1995, 181, 1673-1682

Yu, W. et al. Cancer Res., 1999, 59, 953-961

We claim:

1. A method for treatment of pemphigus characterized by keratinocyte acantholysis, consisting essentially of administering to a patient in need of such treatment an effective amount of a monoclonal human antibody or an antigen-binding fragment thereof which binds to human Fas ligand protein (FasL), wherein said monoclonal antibody comprises at least one heavy chain variable region and at least one light chain variable region,
wherein the amino acid sequences of the complementary determining regions (CDRs) of the heavy chain are:
($a_1$) CDR H1: Arg His Gly Ile Thr (SEQ ID NO: 13)
($b_1$) CDR H2: Trp Ile Asn Ala Tyr Asn Gly Asn Thr Asn Tyr Ala Gln Lys Val Gln Gly (SEQ ID NO: 15) and
($c_1$) CDR H3: Glu Thr Met Val Arg Gly Val Pro Leu Asp Tyr (SEQ ID NO: 17), and the amino acid sequences of the complementary determining regions (CDRs) of the light chain are:
($a_3$) CDR L1: Arg Ala Ser Gln Ser Val Ser Ser Ser Tyr Leu Ala (SEQ ID NO: 19),
($b_3$) CDR L2: Gly Ala Ser Ser Arg Ala Thr (SEQ ID NO: 20), and
($c_3$) CDR L3: Gln Gln Tyr Gly Ser Ser Pro Trp Thr (SEQ ID NO: 21),
wherein said monoclonal antibody or fragment thereof binds to human FasL.

2. A method for the treatment of pemphigus characterized by keratinocyte acantholysis, consisting essentially of administering to a patient in need of such treatment an effective amount of:
(i) the variable domains of a monoclonal antibody or an antigen-binding fragment thereof that binds to human Fas ligand protein (FasL), wherein the monoclonal antibody comprises the light chain variable region and the heavy chain variable region of the antibody produced by the hybridoma cell line deposited under Accession No. ATCC PTA-4017, said light chain variable region comprising SEQ ID NO:23, and said heavy chain variable region comprising SEQ ID NO:24, or
(ii) a monoclonal antibody or an antigen-binding fragment thereof which binds to human FasL and antagonistically binds to the same epitope of human FasL as the antibody or fragment thereof defined in (i).

3. The method according to claim 1, wherein the antibody or an antigen-binding fragment thereof is a partially or a fully humanized antibody or a fragment thereof, or a partially or a fully humanized single chain antibody or a fragment thereof.

4. The method according to claim 1, wherein the pemphigus is characterized by the activation of an apoptotic pathway or the cleavage of desmoglein.

5. The method according to claim 1, wherein the patient is a human patient.

6. The method according to claim 1, further comprising administering at least one additional therapeutically effective drug for treatment of pemphigus.

7. The method according to claim 6, wherein said at least one additional drug is an immunosuppressive drug.

8. The method according to claim 2, wherein the antibody or an antigen-binding fragment thereof is selected from a partially or fully humanized antibody, a partially of fully humanized single chain antibody or a fragment thereof.

9. The method according to claim 2, wherein the pemphigus is characterized by the activation of an apoptotic pathway or the cleavage of desmoglein.

10. The method according to claim 2, wherein the patient is a human patient.

11. The method according to claim 2, further comprising administering at least one additional therapeutically effective drug for treatment of said skin disease.

12. The method according to claim 11, wherein said at least one additional drug is an immunosuppressive drug.

13. The method of claim 7, wherein the immunosuppressive drug is a steroid.

14. The method of claim 12, wherein the immunosuppressive drug is a steroid.

* * * * *